US012606619B2

(12) United States Patent
Sui et al.

(10) Patent No.: US 12,606,619 B2
(45) Date of Patent: Apr. 21, 2026

(54) HUMAN MONOCLONAL ANTIBODIES AGAINST TIGIT FOR IMMUNE RELATED DISEASES

(71) Applicant: HUAHUI HEALTH LTD., Beijing (CN)

(72) Inventors: Jianhua Sui, Beijing (CN); Fang Yang, Beijing (CN); Linlin Zhao, Beijing (CN); Zhizhong Wei, Beijing (CN)

(73) Assignee: HUAHUI HEALTH LTD., Beijing (CN)

( * ) Notice: Subject to any disclaimer, the term of this patent is extended or adjusted under 35 U.S.C. 154(b) by 641 days.

(21) Appl. No.: 18/145,309

(22) PCT Filed: Jun. 23, 2021

(86) PCT No.: PCT/CN2021/101901

§ 371 (c)(1),
(2) Date: Dec. 22, 2022

(87) PCT Pub. No.: WO2021/259335

PCT Pub. Date: Dec. 30, 2021

(65) Prior Publication Data

US 2023/0272067 A1 Aug. 31, 2023

(30) Foreign Application Priority Data

Jun. 24, 2020 (WO) ................ PCT/CN2020/098133

(51) Int. Cl.
*C07K 16/28* (2006.01)
*A61P 35/00* (2006.01)

(52) U.S. Cl.
CPC .............. *C07K 16/28* (2013.01); *A61P 35/00* (2018.01); *C07K 16/2803* (2013.01); *C07K 16/2818* (2013.01); *C07K 16/2827* (2013.01); *C07K 2317/622* (2013.01)

(58) Field of Classification Search
CPC ........................... C07K 16/28; C07K 16/2803; C07K 16/2818; C07K 16/2827; C07K 2317/622; C07K 14/70503; C07K 2317/21; C07K 2317/56; C07K 2317/732; C07K 2317/734; C07K 2317/76; C07K 2317/92; A61P 35/00; A61K 2039/505; A61K 2039/507; A61K 2039/545; Y02A 50/30
See application file for complete search history.

(56) References Cited

U.S. PATENT DOCUMENTS

2016/0355589 A1 12/2016 Williams et al.
2018/0371083 A1 12/2018 Williams et al.

FOREIGN PATENT DOCUMENTS

CN       107148430 A    9/2017
CN       109734806 A    5/2019
CN       111196852 A    5/2020
WO    WO 2016/028656 A1    2/2016

OTHER PUBLICATIONS

African Journal of Biotechnology, 10(79):18294-18302, 2011 (Year: 2011).*
Annu. Rev. Biophys. Biophys. Chem., 16: 139-159, 1987 (Year: 1987).*
J. Immunol. Methods, 251(1-2): 137-149, 2001 (Year: 2001).*
McKay Brown et al., Tolerance to Single, but Not Multiple, Amino Acid Replacements in Antibody VH CDR2, *The American Association of Immunologist*, 1996, 156: pp. 3285-3291.
32nd Annual Meeting and Pre-Conference Programs of the Society for Immunotherapy of Cancer (SITC 2017): Part Two, *Journal for Immuno Therapy of Cancer*, vol. 5 Supplement 2, 2017.
Extended European Search Report of EP 21829075.7, Dec. 12, 2024, 12 pages.
Gao, "Generation and Characterization of Polyclonal Antibodies against Mouse TIGIT by DNA-based Immunization," Chinese Doctoral Dissertations & Master's Theses Full-Text Database (Master) Medicine and Health Sciences, No. 07, 2013, 52 pages.
Harjunpää et al., "TIGIT as an emerging immune checkpoint," Clinical and Experimental Immunology, Epub 2019, 200(2):108-119.
International Search Report of International Application No. PCT/CN2021/101901, Sep. 27, 2021, 6 pages.

* cited by examiner

*Primary Examiner* — Nelson B Moseley, II
*Assistant Examiner* — Josephine K Darpolor
(74) *Attorney, Agent, or Firm* — Merchant & Gould P.C.; Daniel J. Pereira

(57) ABSTRACT

The present invention relates to anti-TIGIT antibodies and antigen-binding fragments thereof that bind to both human TIGIT and mouse TIGIT. The present application also provides are nucleotides encoding the antibodies or fragments thereof, compositions or combinations comprising the antibodies or fragments thereof, and uses of the antibodies or fragments thereof in treatment of immune-related disease such as cancers and viral infection.

21 Claims, 16 Drawing Sheets

Specification includes a Sequence Listing.

```
              10           20           30           40           50           60
               |            |            |            |            |            |
hTIGIT-ECD   MTGTIETTGNISAEKGGSIILQCHLSSTTAQVTQVNWEQQDQLLAICNADLGWHISPSFKDRVA
mTIGIT-ECD   ---..D.KR.....E...V.....F..D..E....D.K........YSV.....VASV.S...V 70           80           90          100          110
               |            |            |            |            |
hTIGIT-ECD   PGPGLGLTLQSLTVNDTGEYFCIYHTYPDGTYTGRIFLEVLESSVAEHGARFQIP
mTIGIT-ECD   ...S....F....M........T.....G.I.K.....K.Q.....QFQTAPLGG
```

HUMAN MONOCLONAL ANTIBODIES AGAINST TIGIT FOR IMMUNE RELATED DISEASES

This application is a U.S. National Stage Application under 35 U.S.C. § 371 of International Patent Application No. PCT/CN2021/101901 filed on Jun. 23, 2021, which claims the benefit of priority of International Patent Application No. PCT/CN2020/098133 filed on Jun. 24, 2020. The foregoing applications are incorporated by reference herein in their entireties.

FIELD OF THE INVENTION

Described herein are isolated antibodies or antigen-binding fragments thereof that bind to TIGIT and block the function of TIGIT, specifically block the interaction of TIGIT with its ligand CD155. The present application also provides use of said anti-TIGIT antibodies or antigen-binding fragments thereof in treating immune related diseases, such as cancers and virus infections.

SEQUENCE LISTING

The Sequence Listing provided in the ASCII file named "CR12807HHH33CN-2nd PCT-EN sequence listing.txt" with a size of 28,863 bytes, which was created on Dec. 16, 2022 and filed herewith, is incorporated by reference in its entirety.

BACKGROUND OF THE INVENTION

Immunotherapies have emerged as extremely potent modalities for treating various cancers. One of the most impactful approaches is based on the blockade of immune checkpoint receptors or ligands.

TIGIT, a member of the poliovirus receptor (PVR)/nectin family, is an immunoreceptor mainly expressed on activated T cells, memory T cells, NK cells, and a subset of T regulatory cells (Tregs) (Johnston, R. J. et al., 2014. *Cancer cell* 26: 923-937; Boles, K. S. et al., 2009. *European journal of immunology* 39: 695-703; Yu, X., K. et al., 2009. *Nature immunology* 10: 48-57; and Levin, S. D. et al., 2011. *European journal of immunology* 41: 902-915). Studies have shown that TIGIT$^{-/-}$ mice were more susceptible to immunization-induced autoimmunity (Levin S. D. et al., 2011, supra; Joller, N. et al., 2011. *J Immunol* 186: 1338-1342.), supporting that TIGIT functions as an inhibitory receptor in maintaining immune homeostasis. TIGIT binds its high affinity cognate ligand CD155 (also known as PVR), which is expressed on antigen-presenting cells (APCs), and this binding inhibits immune responses via T cells and APCs, as well as through NK cells (Joller, N. et al., 2011, supra; Stanietsky, N. et al., 2009. *Proceedings of the National Academy of Sciences of the United States of America* 106: 17858-17863). TIGIT has also been shown to compete with CD226 for binding to CD155 (Yu, X. et al., 2009, supra), thus counterbalancing CD226-mediated co-stimulatory T cell signaling (Johnston, R. J. et al., 2014, supra), which is reminiscent of the function of CTLA-4 to counterbalance CD28's costimulatory function (Egen, J. G. et al., 2002. *Nature immunology* 3: 611-618.).

In cancer contexts, TIGIT is known to be upregulated by tumor-infiltrated T cells, and given that CD155 is highly expressed by both human and mouse tumors and tumor-infiltrating myeloid cells (Martinet, L., and M. J. Smyth. 2015. *Nat Rev Immunol* 15: 243-254; Chan, C. J. et al., 2014.

*Nature immunology* 15: 431-438; Blake, S. J. et al., 2016. *Clinical cancer research* 22: 5183-5188; Li, X. Y et al., 2018. *J Clin Invest* 128: 2613-2625; Kurtulus, S. et al., 2015. *J Clin Invest* 125: 4053-4062). It has been proposed that TIGIT might inhibit anti-tumor immune responses via multiple, sequential steps (Manieri, N. A. et al., 2017. *Trends Immunol* 38: 20-28): first inhibiting NK cell-mediated tumor cell killing as well as tumor antigen release; then inducing tolerogenic dendritic cells and suppressing CD8$^+$ T cell function via TIGIT$^+$ Tregs; and finally directly inhibiting CD8$^+$ T cell effector functions, ultimately preventing the elimination of cancer cells. Therefore TIGIT is considered to be a key inhibitor in cancer immunity (Manieri, N. A. et al., 2017, supra; Dougall, W. C. et al., 2017. *Immunol Rev* 276: 112-120), and targeting TIGIT is viewed as a promising approach for developing cancer immunotherapies.

Anti-TIGIT antibodies have shown therapeutic effects in several murine cancer models, and there several antibodies now under assessment in human clinical trials (Burugu, S. et al., 2018. *Semin Cancer Biol* 52: 39-52.). Despite these promising medical results, the scientific understanding of the mechanism(s) through which these anti-TIGIT antibodies confer their anti-tumor actions remain unclear, which limits efforts to develop more efficacious antibodies or combinations, as well as clinical efforts to identify which patient populations may benefit from such treatment.

Accordingly, efforts are still needed to explore the mechanism underlying the function of anti-TIGIT antibodies so as to develop improved anti-TIGIT antibodies suitable for therapeutic use.

SUMMARY OF THE INVENTION

All references, including scientific publications, patent application publications and patent publications, are incorporated herewith in their entity for all purposes.

By cross-selection and screening of a large phage display antibody library using both extracellular domain (ECD) of human TIGIT (hTIGIT-ECD; Uniprot ID Q495A1) and mouse TIGIT (mTIGIT-ECD; Uniprot ID P86176) as targets, a panel of human monoclonal antibodies with blocking activities against TIGIT and CD155 interaction were identified. Among them, T4 Ab and hm7 Ab showed higher binding affinity to both hTIGIT and mTIGIT, and better blocking activities than other Abs. Optimization of both T4 Ab and hm7 Ab by chain shuffling approach led to more potent Abs with even higher binding affinity, thus completing the invention. In addition, it was found that the anti-TIGIT antibodies of the present application possess Fc-mediated effector functions in addition to their function of blocking the binding of TIGIT to its ligand. Moreover, the anti-TIGIT antibodies of the present application were also found to be capable of inducing cross-protective and durable immune memory effect, rendering them suitable for therapeutic use.

In the first aspect, the present disclosure provides an isolated antibody or an antigen-binding fragment thereof which binds to both human TIGIT (hTIGIT) and mouse TIGIT (mTIGIT). In one embodiment, the antibody or the antigen-binding fragment thereof comprising:

(1) a heavy chain variable domain (VH) comprising an HCDR1 (heavy chain complementarity-determining region 1) having the amino acid sequence of SEQ ID NO: 4, an HCDR2 having the amino acid sequence of SEQ ID NO: 5, and an HCDR3 having the amino acid sequence of SEQ ID NO: 6; and/or a light chain variable domain (VL) comprising an LCDR1 (light chain complementarity-determining region 1) having the amino acid sequence of SEQ ID NO: 9, an LCDR2 having the amino acid sequence of SEQ ID NO: 10, and an LCDR3 having the amino acid sequence of SEQ ID NO: 11;

(2) a heavy chain variable domain (VH) comprising an HCDR1 having the amino acid sequence of SEQ ID NO: 18, an HCDR2 having the amino acid sequence of SEQ ID NO: 19, and an HCDR3 having the amino acid sequence of SEQ ID NO: 20; and/or a light chain variable domain (VL) comprising an LCDR1 having the amino acid sequence of SEQ ID NO: 23, an LCDR2 having the amino acid sequence of SEQ ID NO: 24, and an LCDR3 having the amino acid sequence of SEQ ID NO: 25;

(3) a heavy chain variable domain (VH) comprising an HCDR1 having the amino acid sequence of SEQ ID NO: 18, an HCDR2 having the amino acid sequence of SEQ ID NO: 19, and an HCDR3 having the amino acid sequence of SEQ ID NO: 20; and/or a light chain variable domain (VL) comprising an LCDR1 having the amino acid sequence of SEQ ID NO: 30, an LCDR2 having the amino acid sequence of SEQ ID NO: 31, and an LCDR3 having the amino acid sequence of SEQ ID NO: 32;

(4) a heavy chain variable domain (VH) comprising an HCDR1 having the amino acid sequence of SEQ ID NO: 4, an HCDR2 having the amino acid sequence of SEQ ID NO: 5, and an HCDR3 having the amino acid sequence of SEQ ID NO: 6; and/or a light chain variable domain (VL) comprising an LCDR1 having the amino acid sequence of SEQ ID NO: 1, an LCDR2 having the amino acid sequence of SEQ ID NO: 2, and an LCDR3 having the amino acid sequence of SEQ ID NO: 3; or (5) a heavy chain variable domain (VH) comprising an HCDR1 having the amino acid sequence of SEQ ID NO: 18, an HCDR2 having the amino acid sequence of SEQ ID NO: 19, and an HCDR3 having the amino acid sequence of SEQ ID NO: 20; and/or a light chain variable domain (VL) comprising an LCDR1 having the amino acid sequence of SEQ ID NO: 15, an LCDR2 having the amino acid sequence of SEQ ID NO: 16, and an LCDR3 having the amino acid sequence of SEQ ID NO: 17.

In a more specific embodiment, the isolated antibody or antigen-binding fragment thereof which binds to both human TIGIT (hTIGIT) and mouse TIGIT (mTIGIT) comprises (1) a heavy chain variable domain (VH) comprising an amino acid sequence having at least 95%, 96%, 97%, 98%, 99% or 100% identity to SEQ ID NO: 8; and/or a light chain variable domain (VL) comprising an amino acid sequence having at least 95%, 96%, 97%, 98%, 99% or 100% identity to SEQ ID NO: 12;

(2) a heavy chain variable domain (VH) comprising an amino acid sequence having at least 95%, 96%, 97%, 98%, 99% or 100% identity to SEQ ID NO: 27; and/or a light chain variable domain (VL) comprising an amino acid sequence having at least 95%, 96%, 97%, 98%, 99% or 100% identity to SEQ ID NO: 26; or (3) a heavy chain variable domain (VH) comprising an amino acid sequence having at least 95%, 96%, 97%, 98%, 99% or 100% identity to SEQ ID NO: 34; and/or a light chain variable domain (VL) comprising an amino acid sequence having at least 95%, 96%, 97%, 98%, 99% or 100% identity to SEQ ID NO: 33.

In one embodiment, the isolated antibody or antigen-binding fragment thereof which binds to both human TIGIT (hTIGIT) and mouse TIGIT (mTIGIT) comprises a heavy chain variable domain (VH) comprising an amino acid sequence of SEQ ID NO: 8; and/or a light chain variable domain (VL) comprising an amino acid sequence of SEQ ID NO: 7.

In a more specific embodiment, the isolated antibody or antigen-binding fragment thereof which binds to both human TIGIT (hTIGIT) and mouse TIGIT (mTIGIT) comprises (1) a heavy chain variable domain (VH) comprising an amino acid sequence of SEQ ID NO: 8; and/or a light chain variable domain (VL) comprising an amino acid sequence of SEQ ID NO: 12;

(2) a heavy chain variable domain (VH) comprising an amino acid of SEQ ID NO: 27; and/or a light chain variable domain (VL) comprising an amino acid sequence of SEQ ID NO: 26;

(3) a heavy chain variable domain (VH) comprising an amino acid sequence of SEQ ID NO: 34; and/or a light chain variable domain (VL) comprising an amino acid sequence of SEQ ID NO: 33;

(4) a heavy chain variable domain (VH) comprising an amino acid sequence of SEQ ID NO: 8; and/or a light chain variable domain (VL) comprising an amino acid sequence of SEQ ID NO: 12; or (5) a heavy chain variable domain (VH) comprising an amino acid of SEQ ID NO: 22; and/or a light chain variable domain (VL) comprising an amino acid sequence of SEQ ID NO: 21.

In a more specific embodiment, the antibody or antigen-binding fragment thereof comprises (1) a heavy chain variable domain comprising an amino acid sequence of SEQ ID NO: 8, and a light chain variable domain as shown in FIG. 6 of an antibody selected from the group consisting of IGKV1-39, T4, 1-44, 1-48, 1-60, 1-66, 1-93, 3-5, 3-12, 3-17, 3-96, and T4M;

(2) a heavy chain variable domain selected from the group consisting of IGHV3-23, IGHV3-30, hm7, hm7-3-23, and hm7-3-30 as shown in FIG. 10, and a light chain variable domain as shown in FIG. 9 of an antibody selected from the group consisting of IGLV2-11, IGLV2-14, hm7, Tm1, Tm3, Tm4, Tm5, Tm6, Tm7, Tm8, Tm9, Tm10, Tm11, Tm12, Tm13, Tm14, Tm15, Tm17, Tm18, Tm19, CS19, CS19ME, and CS19ME-N.

In one embodiment, the anti-TIGIT antibody is a human antibody. In one embodiment, the anti-TIGIT antibody is a human monoclonal antibody (mAb).

In one embodiment, the anti-TIGIT antibody is a Fab, F(ab')2, Fv, a single chain Fv (ScFv) or comprised as a domain in a bispecific or trispecific antibody.

In one embodiment, the anti-TIGIT antibody comprises a heavy chain constant region of the subclass of IgG1, IgG2, IgG3, IgG4 or a variant thereof, and a light chain constant region of the type of kappa or lambda or a variant thereof. In a preferred embodiment, the anti-TIGIT antibody comprises a heavy chain constant region of IgG1.

In one embodiment, the anti-TIGIT antibody is an isolated antibody. In one embodiment, the anti-TIGIT antibody is a recombinant antibody.

In one embodiment, the anti-TIGIT antibody of the present application possesses Fc-mediated effector function. In one preferred embodiment, the anti-TIGIT antibody of the present application possesses increased Fc-mediated effector function.

In one embodiment, the anti-TIGIT antibody of the present application is further modified by changing the Fc region so as to (1) enhance ADCC function, (2) enhance ADCP function; and/or (3) reduce or eliminate CDC function, as compared to the antibody without such modification. Preferably, the Fc-modified variant of the anti-TIGIT antibody of the present application has enhanced ADCC function, enhanced ADCP function, and reduced or no CDC function, as compared to the anti-TIGIT antibody of the present application before the modification.

In one embodiment, the anti-TIGIT antibody of the present application is an afucosylated antibody. In one embodiment, the afucosylated antibody has increased effector functions as compared to its fucosylated counterpart.

In one embodiment, the anti-TIGIT antibody of the present application induces immune memory effect. In a more specific embodiment, the immune memory effect induced by the anti-TIGIT antibody of the present application creates cross-tumor immunity.

In the second aspect, the present disclosure provides a composition, e.g., a pharmaceutical composition, comprising the anti-TIGIT antibody or antigen-binding fragment of the first aspect of the present application, and a pharmaceutically acceptable excipient. In a preferred embodiment, the pharmaceutical composition comprises a therapeutically efficient amount of the anti-TIGIT antibody or antigen-binding fragment.

In the third aspect, the present disclosure provides a kit comprising the anti-TIGIT antibody or antigen-binding fragment of the first aspect of the present application, or the composition of the second aspect of the present application. In a preferred embodiment, the kit comprises a therapeutically efficient amount of the anti-TIGIT antibody or antigen-binding fragment.

In the fourth aspect, the present disclosure provides a method for preventing or treating an immune-related condition or disease, comprising administering to a subject in need thereof an therapeutically effective amount of the anti-TIGIT antibody or antigen-binding fragment of the first aspect of the present application, or the pharmaceutical composition of the second aspect of the present application. In a specific embodiment, the immune-related condition or disease is cancer or viral infection, such as chronic viral infection.

In a fifth aspect, the present disclosure provides a method for preventing recurrence of an immune-related condition or disease such as cancer, comprising administering to a subject in need thereof an therapeutically effective amount of the anti-TIGIT antibody or antigen-binding fragment of the first aspect of the present application, or the pharmaceutical composition of the second aspect of the present application. In a specific embodiment, the disease or disorder is cancer.

In the sixth aspect, the present disclosure provides use of the antibody or antigen-binding fragment of the first aspect of the present application, or the pharmaceutical composition of the second aspect of the present application for treating various conditions or diseases described herein, or for preventing recurrence of various conditions or diseases described herein.

In the seventh aspect, the present disclosure provides use of the anti-TIGIT antibody or antigen-binding fragment of the first aspect of the present application, or the pharmaceutical composition of the second aspect of the present application in the manufacture of a medicament for treating various conditions or diseases described herein, or for preventing recurrence of various conditions or diseases described herein.

In the eighth aspect, the present disclosure provides isolated nucleic acid encoding the anti-TIGIT antibody or fragment of the first aspect. In a more specific embodiment of this aspect, the isolated nucleic acid encoding the anti-TIGIT antibody or fragment thereof comprising (1) nucleotide sequence of SEQ ID NO: 14, and/or a nucleotide sequence having at least 95%, 96%, 97%, 98%, 99% or 100% identity to the nucleotide sequence of SEQ ID NO: 13;

(2) a nucleotide sequence having at least 95%, 96%, 97%, 98%, 99% or 100% identity to the nucleotide sequence of SEQ ID NO: 29, and/or a nucleotide sequence having at least 95%, 96%, 97%, 98%, 99% or 100% identity to the nucleotide sequence of SEQ ID NO: 28; or (3) a nucleotide sequence having at least 95%, 96%, 97%, 98%, 99% or 100% identity to the nucleotide sequence of SEQ ID NO: 36, and/or a nucleotide sequence having at least 95%, 96%, 97%, 98%, 99% or 100% identity to the nucleotide sequence of SEQ ID NO: 35.

In the ninth aspect, the present disclosure provides an expression vector comprising the nucleic acid of the eighth aspect.

In the tenth aspect, the present disclosure provides a host cell comprising the nucleic acid of the eighth aspect or the expression vector of the ninth aspect.

BRIEF DESCRIPTION OF THE DRAWINGS

FIGS. 2A-B show the binding of anti-TIGIT Abs to hTIGIT and mTIGIT. A) Flow cytometry analysis. B) Single-cycle kinetic analyses using Biacore T200.

FIGS. 16A-C show ADCP effector functions induced by anti-TIGIT Abs via macrophages. Raji-hTIGIT target cells were labeled with CFSE fluorescent dye prior to mixing with mouse bone marrow-derived macrophages stained with F4/80-Alexa Fluor 633 Ab. The E:T ratio was 1:2. ADCP activity was monitored via fluorescence microscopy. The phagocytosis index was determined as the number of CFSE-positive target cells per 100 macrophages. Detection of ADCP responses mediated by T4 mIgG Abs (A), CS19ME3-30-N mIgG Abs (B), or hIgG Abs (C) were performed. ("ns": no significance; ****P<0.0001).

FIGS. 17A-D show CDC effector functions induced by anti-TIGIT Abs. Raji-hTIGIT target cells were incubated with anti-TIGIT Abs in the presence of 5% rabbit complement sera. CDC activity was measured using Lactate dehydrogenase (LDH) release with three replicates. Abs were tested at 15-20 µg/ml. Detection of CDC responses mediated by T4 mIgG Abs (A), CS19ME3-23 mIgG Abs (B), or hIgG Abs (C and D) were performed. ("ns": no significance; ****P<0.0001).

FIGS. 18A-F show the potent anti-tumor activities of the anti-TIGIT Abs depending on Fc-mediated effector functions in mouse models. A) The expression of mCD155 on CT26, A20, or 4T1 cell lines. B—C) Anti-tumor activities of CS19ME3-30-N-mIgG2a, T4-hIgG1, or T4-mIgG2a in CT26 tumor models. D) Anti-tumor activities of T4-mIgG2a in A20 or 4T1 tumor models. E-F) Anti-tumor activities of T4 or CS19ME3-23 Ab and their Fc variants in CT26 and A20 tumor models. The time points for antibody administration are marked by arrows. Tumor volumes are shown as mean±SEM.

FIGS. 19A-D show the results of pharmacokinetic profile of the anti-TIGIT Abs in mice. A-B) The log serum Ab concentration vs. time profile of a single administration of T4 (A) or CS19ME3-23 Abs (B) (10 mg/kg) in BALB/c mice is shown. C-D) The serum Ab concentration vs. time profile of a single administration of CS19ME3-30-N-hIgG1 Ab (5 mg/kg) in C57 WT (C) or C57-hFcRn (D) mice is shown. Data are presented as mean values±SEM.

FIGS. 20A-K show the results of depletion studies of Example 9. A) T cells are required for an optimal therapeutic effect of T4 Ab. The anti-tumor effect of T4 Ab for treating CT26 tumor was compared in BALB/c (n=5/group) and Nude mice (n=6/group). B-K) Effects of selective immune-cell depletions on T4 Ab's therapeutic efficacy in treating CT26 or A20 tumor. CD4-depleting antibodies (clone GK1.5) or CD8-depleting antibodies (clone 2.43) were used to deplete CD4+ or CD8+ T cells. Anti-Asialo-GM1 polyclonal antibody (Poly21460), anti-Ly6G antibody (1A8 clone) or clodronate liposomes (FormuMax) was used for the depletion of NK cells, neutrophils or macrophages, respectively. Black arrows indicate the administrations of depletion antibodies or clodronate liposomes. T4 Ab treatment (10 mg/kg) is indicated by gray arrows. Tumor volumes over time are shown (n=4-6/group).

Figure 21:
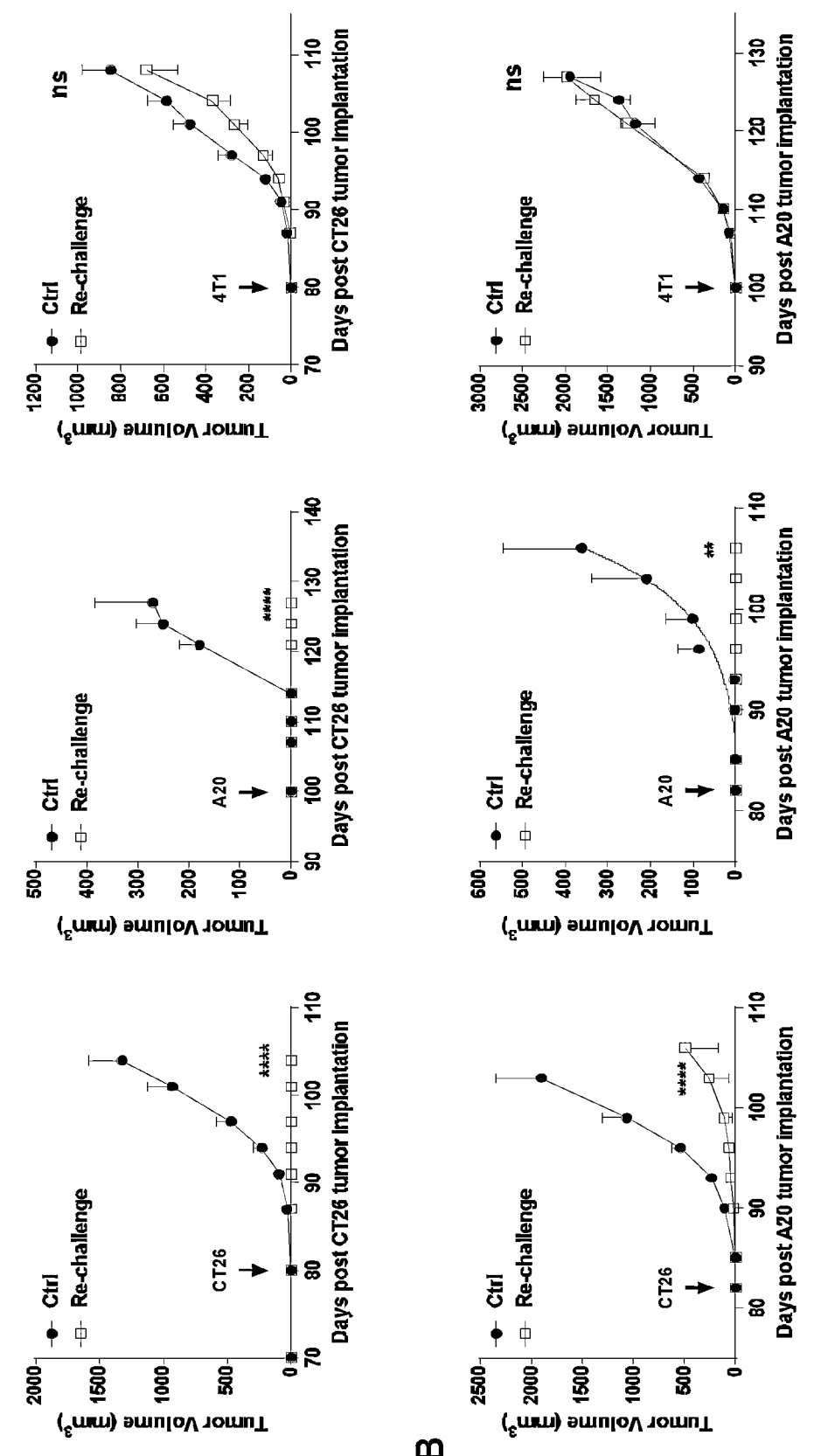

FIGS. 21A-B show the immune memory induced by the treatment with the anti-TIGIT antibodies of the present application. A) CT26-tumor bearing mice cured by T4 Ab treatment were re-challenged with CT26, A20, or 4T1. Arrows indicate the time point of re-challenge. Age-matched naïve mice were included as controls. n=3-5/group. B) A20-tumor bearing mice cured by T4 Ab treatment were re-challenged with A20, CT26, or 4T1. The study was performed similarly as in panel A.

Figure 22:
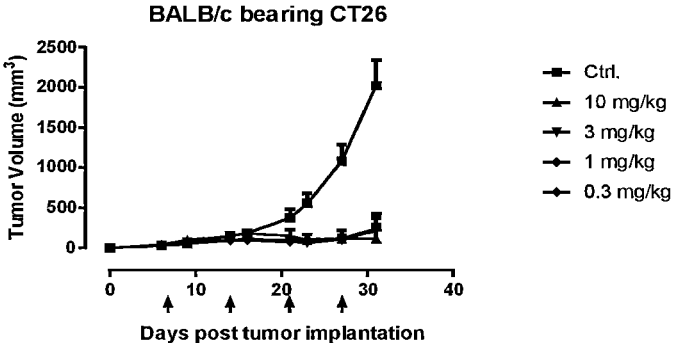

FIG. 22 shows the anti-tumor effect of the anti-TIGIT Ab (CS19ME3-30-N-hIgG1-afuco) at different doses. The time points of dosing are marked by arrows. Tumor volumes are shown as mean±SEM.

FIGS. 23A-C show the synergistic anti-tumor effect of the anti-TIGIT Abs and anti-PD-1 (or anit-PD-L1) Ab. A) A comparison of anti-tumor effect in C57 mice bearing MC38 obtained by no-treatment control group, anti-TIGIT Ab treatment group (CS19ME3-30-N-mIgG2a, 10 mg/kg), anti-mPD-1 Ab treatment group (RMP1-14, 3 mg/kg) and combined treatment group. B) and C) A comparison of anti-tumor effect in BALB/c mice bearing CT26 randomized into the following groups based on similar mean CT26 tumor volumes (120-270 mm³): no-treatment control group, anti-TIGIT Ab treatment group (CS19ME3-30-N-hIgG1-afuco, 1 mg/kg), anti-mPD-1 Ab treatment group (RMP1-14, 5 mg/kg) or homemade anti-mPD-L1 Ab treatment group (mP4, 10 mg/kg), and combined treatment group. The time points for antibody treatment are marked by arrows. Tumor volumes are shown as mean±SEM.

DETAIL DESCRIPTION OF THE INVENTION

Definitions

Unless specifically defined elsewhere in this document, all other technical and scientific terms used herein have the meaning commonly understood by one of ordinary skill in the art to which this invention belongs.

As used herein, including the appended claims, the singular forms of words such as "a", "an", and "the", include their corresponding plural references unless the context clearly dictates otherwise.

The term "or" is used to mean, and is used interchangeably with, the term "and/or" unless the context clearly dictates otherwise.

In the context of the present disclosure, unless being otherwise indicated, the wording "comprise", and variations thereof such as "comprises" and "comprising" will be understood to imply the inclusion of a stated element, e.g. an amino acid sequence, a nucleotide sequence, a property, a step or a group thereof, but not the exclusion of any other elements, e.g. amino acid sequences, nucleotide sequences, properties and steps. When used herein the term "comprise" or any variation thereof can be substituted with the term "contain", "include" or sometimes "have" or equivalent variation thereof. In certain embodiments, the wording "comprise" also includes the scenario of "consisting of".

Antibody and Antigen-Binding Fragment Thereof

Unless being otherwise indicated, the term "antibody" or "Ab" as used herein encompasses antibodies as well as antibody fragments in the broadest sense, as long as it recognizes and binds to human TIGIT and mouse TIGIT. The antibody of the present application in general refers to a monospecific antibody. But the present application also contemplates an antibody with heterologous specificity (heterospecific) or a multispecific antibody. An "antibody fragment" and "antigen-binding fragment" are interchangeable which means a portion of a full length antibody, usually comprising the binding or variable region for the antigen. Examples of antibody fragments can include Fab, Fab', F(ab')2 and Fv fragments; diabodies; linear antibodies; single-chain antibody molecules; and multi-specific antibodies formed from antibody fragments.

By "specific binding" or "specifically bind to", it means that an antibody exhibits preferential binding to a certain target as compared to other proteins, but this specificity does not require absolute binding specificity. An antibody is considered "specific" for its intended target if its binding is determinative of the presence of the target protein in a sample, e.g. without producing undesired results such as false positives. The antibody or an antigen binding fragment thereof of the present invention will bind to the target protein with an affinity that is at least 2-fold greater, preferably at least 10-fold greater, more preferably at least 20-fold greater, and most preferably at least 100-fold greater than the affinity with non-target proteins. Alternatively or additionally, the antibody or an antigen binding fragment thereof of the present invention will have a binding affinity to its target protein, specifically to both hTIGIT and mTIGIT as represented by a KD value of lower than $1\times10^{-7}$ M, lower than $1\times10^{-8}$ M, lower than $1\times10^{-9}$ M (1 nM), lower than $1\times10^{-10}$ M, lower than $1\times10^{-11}$ M, or even lower than $1\times10^{-12}$ M (1 pM).

The term "human antibody" as used herein means an antibody that comprises human immunoglobulin protein sequences only. A human antibody may contain murine carbohydrate chains if produced in a mouse, in a mouse cell, or in a hybridoma derived from a mouse cell. Similarly, "mouse antibody" means an antibody comprising only mouse or rat immunoglobulin protein sequences, respectively.

The antibody of the present invention specifically binding to human TIGIT also shows cross-reactivity with mouse ortholog of human TIGIT. The term "cross-reactivity" as used herein refers to the ability of an antibody to react with a homologous or orthologous protein derived from other species. The cross-reactivity of an antibody can be determined using any method as known in the art. For example, it can be determined by measurement of binding affinity via surface plasmon resonance (e.g., BIACORE) or a similar technique (e.g. KinExa or OCTET).

The antibody of the present application can be subjected to a purification process to remove unwanted materials, resulting in a purified antibody. Conventional methods for purifying antibodies include but not limited to column chromatography methods, which are well known in the art.

The antibody or the antigen-binding fragment of the present invention can be an isolated antibody. By the term "isolated" it means that the antibodies or antigen-binding fragments are at least partially free of other biological materials or non-biological materials from the cells, cell cultures, growth medium, expression system in which they are produced. Said materials may include nucleic acids, proteins, lipids, carbohydrates, buffer, salt or other material such as cellular debris and growth medium.

The present application also contemplates an antibody or antigen-binding fragment thereof comprising one or more conservative substitutions, as long as the antibody or antigen-binding fragment binds to hTIGIT and mTIGIT, and possesses at least one of the properties of the antibody as described herein. "Conservative substitutions" of amino acids are well known in the art and generally refer to change one an amino acid residue into another amino acid residue having a similar side chain in structure or function.

In the present application, a consensus amino acid sequence of e.g. a variable region or CDR is determined by aligning multiple sequences of related antibodies of the present application and identifying the most frequently shown residue at each position. As a result, a consensus sequence shares high sequence homology to the specific antibodies of the present application which are used to make the alignment. One may contemplate that an antibody comprising variable regions or CDRs different from the consensus sequence only in a few amino acids (less than 30%, less than 25%, less than 20%, less than 15% or less than 10% of the amino acids of the whole sequence), especially at variable positions as shown in the alignments, may have similar properties as the specific antibodies involved in the alignments, and should also be covered by the present application.

The present application also provides an isolated nucleic acid sequence comprising a nucleotide sequence coding for the antibody or fragment thereof the present application. By "isolated nucleic acid" or "isolated polynucleotide", it means a DNA or RNA which is removed from all or a portion of a polynucleotide in which the isolated polynucleotide is found in nature, or is linked to a polynucleotide to which it is not linked in nature. An isolated nucleic acid molecule "comprising" a specific nucleotide sequence may include, in addition to the specified sequence, operably linked regulatory sequences that control expression of the coding region of the recited nucleic acid sequences. Due to the codon degeneracy, one skilled in the art can understand that a specific amino acid sequence can be coded by different nucleotide sequences.

By "effector function", specifically "Fc-mediated effector function", it refers to the effects resulted from the interaction or binding of the Fc region of an antibody with Fc receptors, and includes e.g. binding to C1q on the C1 complex, complement dependent cytotoxicity (CDC), FcγR-mediated effector functions such as antibody dependent cellular cytotoxicity (ADCC) and antibody dependent cell-mediated phagocytosis (ADCP). The antibody of the present application may have effector functions or have no effector function.

As known in the art, the effector functions of an antibody can be modulated by altering the amino acid sequence or post-translational modifications of the Fc and/or constant region of the antibody. It was found that mIgG2a-DLE variant of the antibody of the present application (T4 or CS19ME3-23) showed improved anti-tumor effect as compared to the antibody having wild-type mIgG2a. The mIgG2a-DLE variant showed ADCC and ADCP functions while no CDC function. Accordingly, in a preferred embodiment, the present application relates to an antibody of the first aspect with ADCC and/or ADCP functions but without CDC function; or an Fc variant of the antibody of the first aspect with enhanced ADCC and/or ADCP functions, and reduced or no CDC function.

In the context of the present application, by "immune memory" or "immunological memory", it means that an immune system has established immunity to certain challenges so that it can efficiently respond to a subsequent challenge when it occurs. In specific embodiments of the present application, the immune memory created by the anti-TIGIT antibody of the present application means that administration of the antibody not only reduces the tumor or cancer, but also protects the subject from secondary or recurrent tumor or cancer. More preferably, the immune memory induced by the anti-TIGIT antibodies of the present application provides cross-protection over different types of cancers. That is, when the antibody is used to treat one tumor, cross-protective immune memory is established and protects the subject from developing another tumor which is also responsive to the antibody of the present application.

Therapeutic Uses

The present disclosure provides a method for preventing, treating or preventing recurrence of an immune-related disease, such as cancers and viral infection, e.g. chronic viral infection, comprising administering to a subject in need thereof an therapeutically effective amount of the anti-TIGIT antibody or antigen-binding fragment of the first aspect of the present application, or the pharmaceutical composition of the second aspect of the present application.

The term "therapeutically effective amount" as used herein, refers to the amount of an antibody that, when administered to a subject for treating a disease, or at least one of the clinical symptoms of a disease or disorder, is sufficient to effect such treatment for the disease, disorder, or symptom. The "therapeutically effective amount" can vary with the antibody, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be apparent to those skilled in the art or can be determined by routine experiments. In the case of combination therapy, the "therapeutically effective amount" refers to the total amount of the combination objects for the effective treatment of a disease, a disorder or a condition.

In the context of the present application, by "subject" it refers to an animal, preferably a mammal, e.g., a primate, preferably a higher primate, e.g., a human.

The terms "cancer" or "tumor" herein mean or describe the physiological condition in mammals that is typically characterized by unregulated cell growth. The cancers which can be treated by the antibody of the present application include both solid tumor and hematological malignancy, for example, breast cancer, lymphoma, and colorectal cancer.

The anti-TIGIT antibody of the present application can be used in combination with an additional therapeutic agent, including but not limited to an anti-PD-1 antibody, an anti-PD-L1 antibody, an anti-LAG3 antibody, an anti-TIM3 antibody, an anti-OX40 antibody, and an anti-CTLA4 antibody.

EXAMPLES

Example 1. Generation of Anti-TIGIT Antibodies

This example describes the generation of the anti-TIGIT antibodies of the present application from library screening.

Antigen Targets—TIGIT-ECD and mTIGIT-ECD

Figures 1, 2:
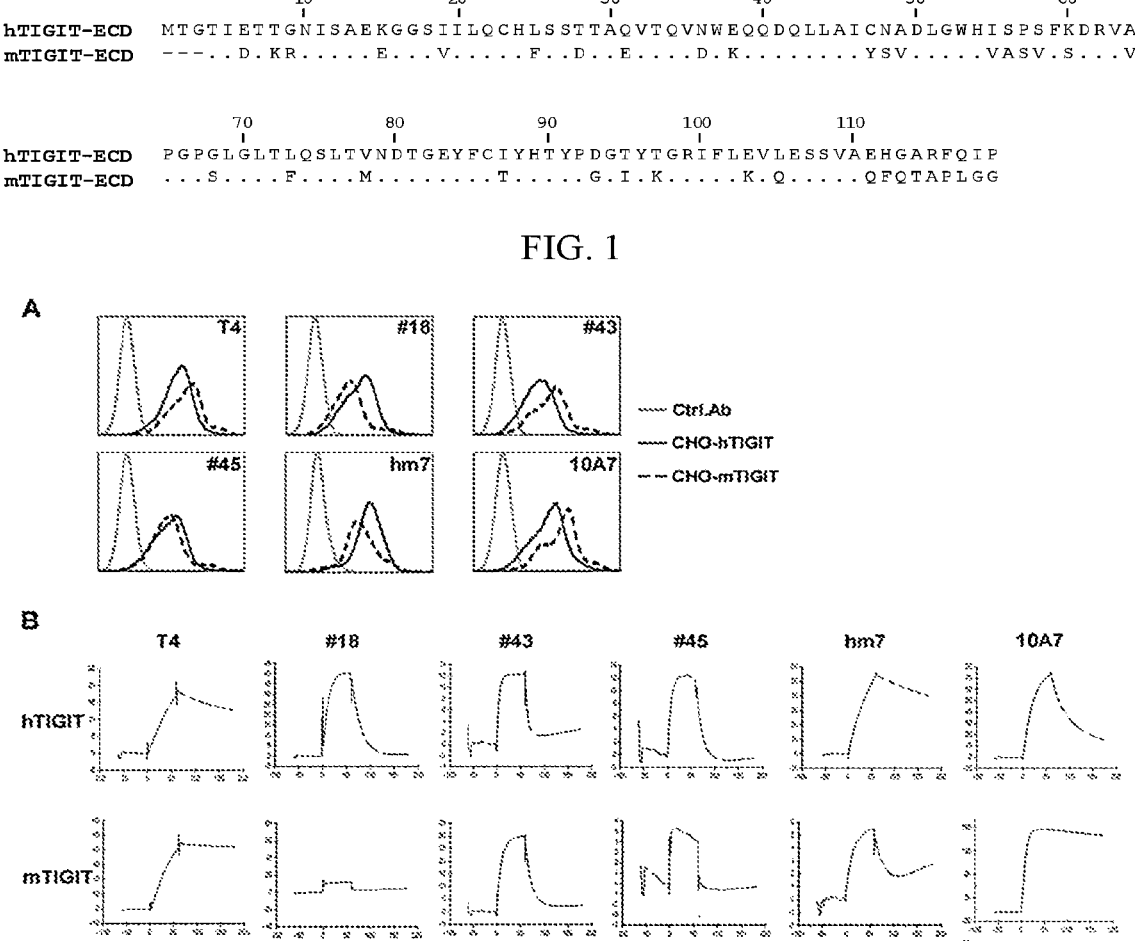
FIG. 1 shows the amino acid alignment of hTIGIT-ECD (human TIGIT extracellular domain) and mTIGIT-ECD (mouse TIGIT extracellular domain), in which the dots denote the positions having identical amino acid residues.

The extracellular domain (ECD) of hTIGIT and mTIGIT were used as targets for library screening. Both ECDs were expressed as biotinylated recombinant fusion proteins. The sequence alignment of hTIGIT-ECD and mTIGIT-ECD is shown in FIG. 1.

Phage Display Antibody Library

A human non-immune scFv (Single-chain variable fragment) antibody library was constructed from peripheral blood mononuclear cells (PBMCs) of 93 healthy donors. The library had a size of a total of $1.1 \times 10^{10}$ members (Li D, et al. A potent human neutralizing antibody Fc-dependently reduces established HBV infections. Elife 2017; 6).

Selection and Screening of Phage Antibody Library

Phage particles expressing scFv on their surface (phage-scFv) were prepared from the library and used for selection of phage-scFvs against the purified antigens. For the first-round selection, the biotinylated hTIGIT-ECD protein was captured on streptavidin-conjugated magnetic M-280 Dyna-beads® (Life Technologies) and then incubated with $1 \times 10^{13}$ phage particles prepared from the library. For the second-round selection, the hTIGIT-ECD-Biotin or mTIGIT-ECD-Biotin protein was captured on M-280 Dynabeads and incubated with phage particles prepared from the first-round selection. For each round of selection, in order to obtain high affinity Abs, the amount of antigen captured onto the magnetic beads was optimized and extensive washing steps were applied. The library selection was repeated twice independently.

Subsequently, single clones were picked and rescued to produce phage-scFvs in the bacterial culture supernatant, and screened for antibodies with binding specificity for both hTIGIT and mTIGIT by enzyme-linked immunosorbent assay (ELISA). Clones that cross-reacted with hTIGIT and mTIGIT were selected based on OD450 (>0.6 for both hTIGIT and mTIGIT). The nucleotide sequences of variable regions of heavy (VH) and light (VL) chain of the clones were sequenced. Their corresponding amino acid sequences were aligned to identify antibodies with different sequences for further characterization.

After the 2 rounds of selection, about 3000 phage-Ab clones were screened for cross-binding activity to both hTIGIT-ECD and mTIGIT-ECD using ELISA, and about 100 clones with cross-binding activity were thusly obtained. These were subsequently converted into hIgG1 format and analyzed for binding to both hTIGIT- and mTIGIT-expressing CHO cells using FACS.

Further Characterization of the Abs with Unique Sequences to Identify the Best Antibody Candidates The antibody clones with unique sequence were either produced as purified phage-scFv particles or full-length human IgG1 s to test their binding activities to CD155 and competitive binding to CD155 by ELISA, FACS, or SPR (Surface Plasmon Resonance). Based on the results of these assays, Abs were ranked according to their binding activity and competitive activity. The top ranked antibodies were chosen for further development.

Preparation of Purified Phage-ScFvs for Binding and Competition Activity Analyses The phage-scFvs in the supernatant of 10-30 mL bacterial culture were precipitated by PEG/NaCl and then quantified by a spectrometer. The phage-scFvs were evaluated for the TIGIT binding activity and activity of blocking the interaction between TIGIT and CD155 by making serial dilution of the phage-Abs and normalizing to the same concentrations.

Preparation of Full-Length IgG1 Antibody

The VH and VL coding sequences of a scFv were separately cloned into antibody heavy chain (HC) expression vector and light chain (LC) expression vector. To produce IgG Ab, 293F (Life Technologies) cells were transiently co-transfected with the two expression plasmids (HC+LC plasmids) at a ratio of 1:1. 3-5 days after transfection, the cell culture supernatant was harvested for purification of IgG Ab by Protein A affinity chromatography (Protein A Sepharose CL-4B, GE Healthcare).

ELISA-Based Binding and Competition Assays

For the ELISA-based binding assay, biotinylated protein antigens were captured with streptavidin (Sigma) coated 96-well plates (Nunc, MaxiSorp™). For phage-scFv based ELISA, serially diluted phage-scFvs were added, and then detected by adding mouse anti-M13-HRP antibody (GE Healthcare). Similar process was performed for full-length human IgG-based ELISA assays. The bound Abs were detected using a mouse anti-human IgG Fc-HRP antibody (Thermo Fisher Scientific).

The ELISA-based competition assays were performed in a manner similar with ELISA-based binding assays, except that the tested Abs were incubated with captured antigens in the presence of competitive ligands, human CD155 and mouse CD155. Briefly, different human IgG1 antibodies at serially diluted concentrations were mixed with 2 μg/mL of the extracellular domain of hCD155 or mCD155 fused with mouse Fc tag (hCD155-mFc or mCD155-mFc) and added to the ELISA plates to compete for the binding to TIGIT with CD155. The signal was measured via ligand detection using HRP-anti-mouse IgG secondary Ab (Thermo F isher Scientific).

FACS-Based Binding and Competition Assays

CHO cell lines (CHO-hTIGIT and CHO-hTIGIT) stably expressing the full length of h/mTIGIT were used in this assay. For cell line construction, an expression plasmid was constructed by inserting the DNA fragment encoding the full-length (Uniprot ID Q495A1) or mTIGIT (Uniprot ID P86176) into vector. The expression plasmid was then transfected into CHO cells, followed by FACS sorting of 10A7 (anti-TIGIT Ab generated by Genetech)-staining positive populations for these stable cell lines.

For FACS-based binding assay, CHO-h/mTIGIT cell lines were incubated with different hIgG1 Abs at 5 μg/mL in 1% BSA/PBS at 4° C. for 1 hour. Then cells were washed three times with PBS containing 1% BSA. Abs binding to cells were detected by adding goat anti-human IgG Fc-FITC Ab (Pierce-Thermo Fisher Scientific).

Binding Kinetic Analysis by Surface Plasmon Resonance (SPR) Technology

Kinetic analyses of the bindings of T4 and T4's Fc variants to the extracellular domain of hTIGIT or mTIGIT were performed on a Biacore T200 instrument (Biacore, GE Healthcare). Anti-hFc Ab (Thermo Fisher) was covalently attached to surfaces of a CMS sensor chip using an amine coupling kit (GE Healthcare). Abs at optimal concentrations were captured on the chip and the analytes (hTIGIT or mTIGIT) were then injected at determined concentrations or at 2-fold serially diluted concentrations. Binding kinetics were evaluated using a 1:1 Langmuir binding model. The association rates (ka), dissociation rates (kd), and affinity constants (KD) were calculated using Biacore T200 evaluation software.

Figures 3, 4:
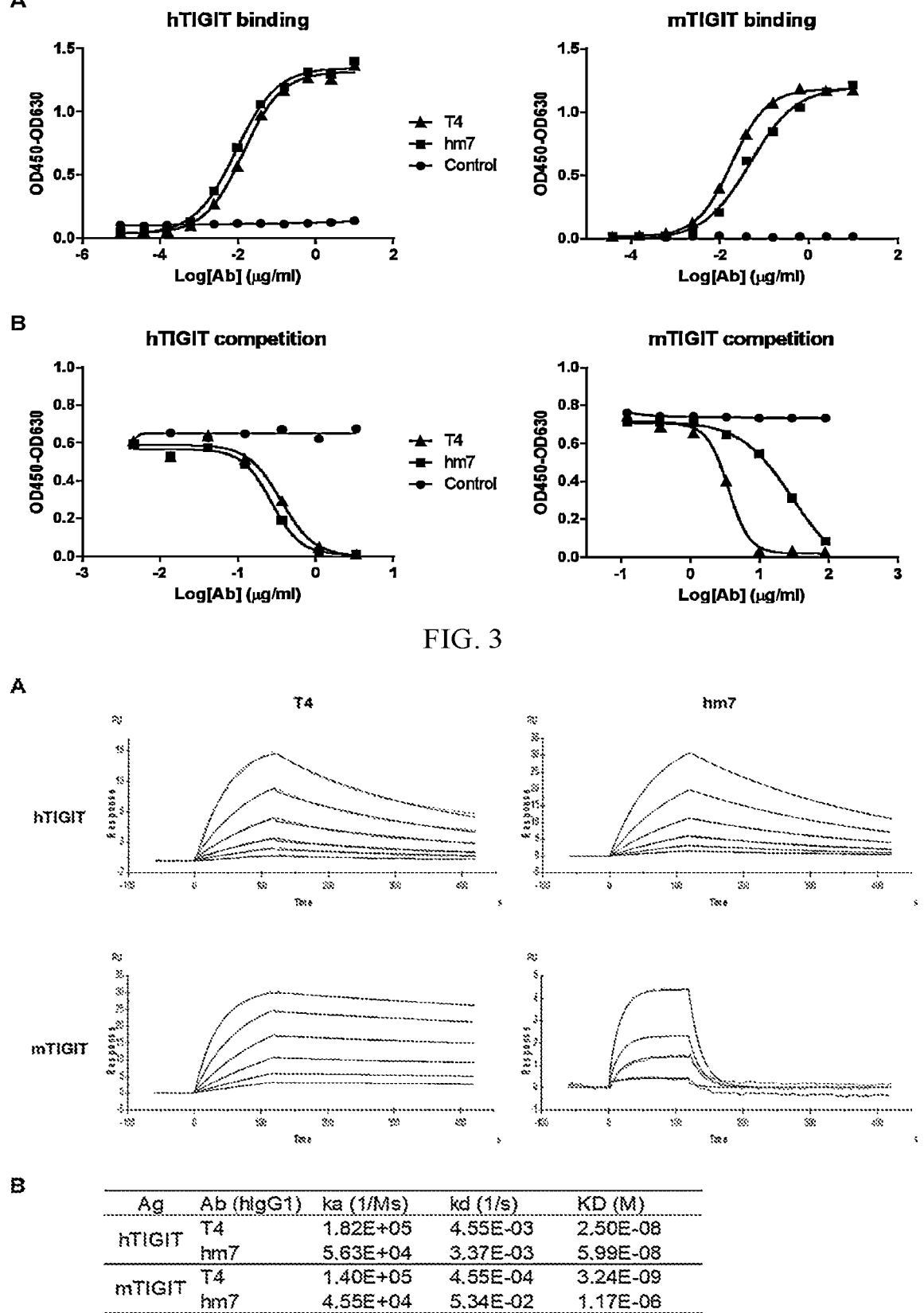
FIGS. 3A-B show the binding and ligand competition activities of anti-TIGIT Abs analyzed by ELISA. A) Binding of T4 and hm7 Abs to purified TIGIT-ECD proteins. B) Ligand competition assays of T4 and hm7 Abs.
FIGS. 4A-B show the binding kinetics of anti-TIGIT Abs to hTIGIT or mTIGIT by SPR. A) Multi-cycle kinetic analyses of the interaction between anti-TIGIT Abs (T4 and hm7) and hTIGIT or mTIGIT using Biacore T200. B) A table listing the values of ka, kd, and KD.

According to FACS-based binding analysis, five clones (T4, #18, #43, #45, and hm7) showed high cross-binding affinity to both CHO-hTIGIT and CHO-mTIGIT cells (FIG. 2A). Owing to their binding kinetics for both hTIGIT and mTIGIT, two top-ranked Abs, T4 and hm7 Abs were selected as the lead candidates (FIG. 2B). These two Abs, T4 and hm7, showed specific binding with both hTIGIT and mTIGIT, and showed competitive activity for TIGIT with its ligands CD155 in ELISA, FACS, or SPR assays (FIGS. 3-4).

Example 2. Improving Binding Affinity of T4 by VL Chain Shuffling

To further improve T4 binding affinity, the present inventors made a VL chain shuffled phage display library, in which VH of T4 was fixed and paired with a library of different Vk (kappa variable light chain) chains. The final library (T4VH/Vk lib) constructed had a size of about $2.8 \times 10^8$.

Figure 5:
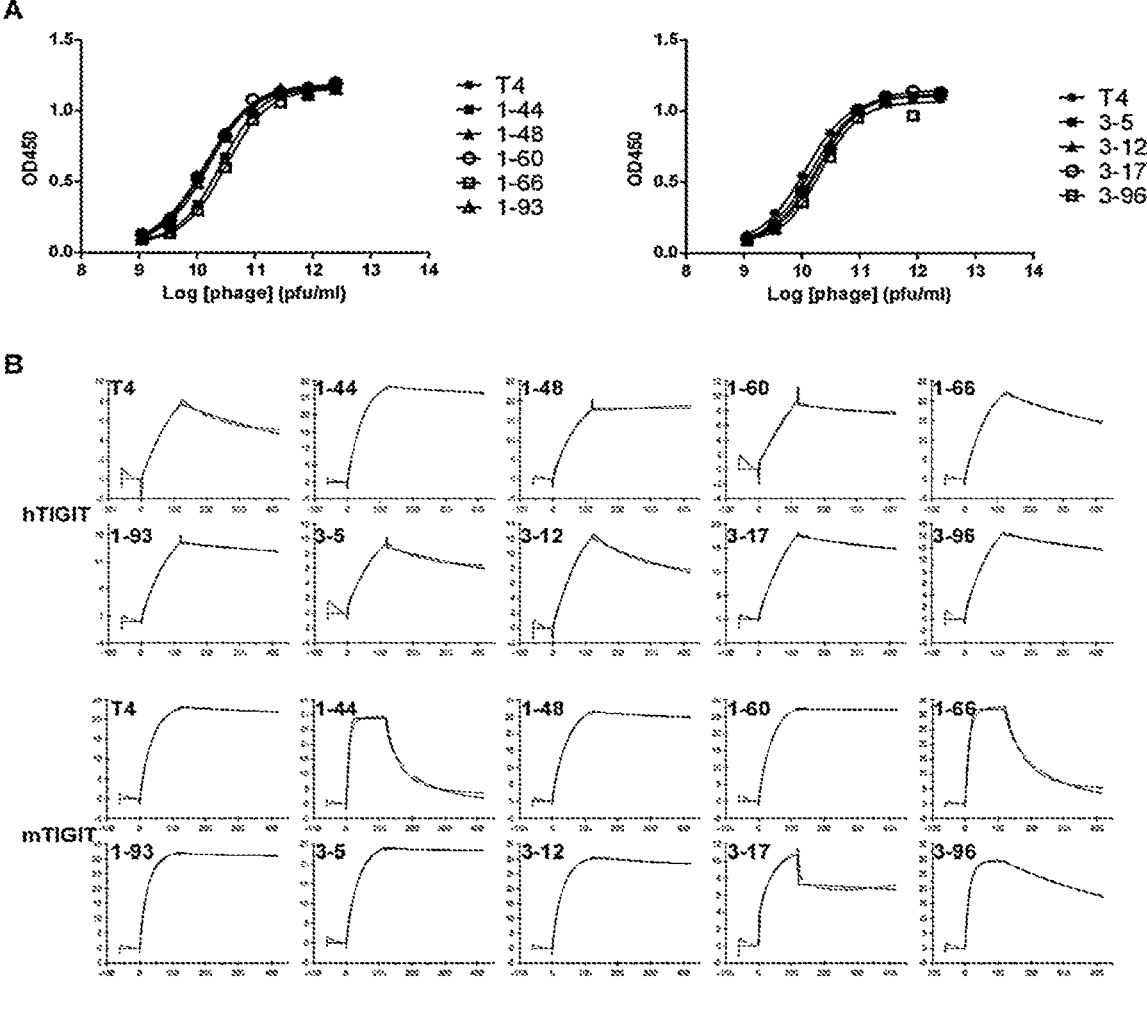
FIGS. 5A-B show the binding analyses of T4 and T4-derived anti-TIGIT Abs to hTIGIT and mTIGIT using ELISA and SPR. A) Binding analyses of the anti-TIGIT Abs to purified TIGIT-ECD proteins (biotinylated hTIGIT-ECD or mTIGIT-ECD). B) Single-cycle kinetic analyses of the interactions between anti-TIGIT Abs to hTIGIT or mTIGIT using Biacore T200.

By using hTIGIT captured on streptavidin-conjugated magnetic M-280 Dynabeads® (Life Technologies) as target, the T4VH/Vk lib was screened for two rounds. 196 clones were screened for binding with hTIGIT using ELISA. Most clones were positive and were picked for sequencing. Nine clones, 1-44, 1-48, 1-60, 1-66, 1-93, 3-5, 3-12, 3-17, and 3-96 with different Vk chain sequences were identified by phage-ELISA. These Abs were converted into full-length human IgG1 and tested for binding to hTIGIT or mTIGIT using Biacore. Among the nine clones, clone 1-48 showed the strongest binding activity to both hTIGIT and mTIGIT than other Abs, as shown in FIG. 5. The VH sequences of these clones are identical, which is SEQ ID NO: 8 and encoded by the nucleotide sequence of SEQ ID NO: 14. The Vk sequences of the these clones are shown in FIG. 6, in which the light chain CDR1, CDR2 and CDR3 (LCDR1, LCDR2 and LCDR3) are amino acids 24-34, amino acids 50-56 and amino acids 89-97, respectively, in the amino acid sequence of respective Vk according to a Kabat system.

TABLE 1

| Sequence information of T4M | | | | |
|---|---|---|---|---|
| Ab | VH nucleotide SEQ ID NO. | VH amino acid SEQ ID NO. | Vk nucleotide SEQ ID NO. | Vk amino acid SEQ ID NO. |
| T4M | 14 | 8 | 13 | 12 |

Figure 6:
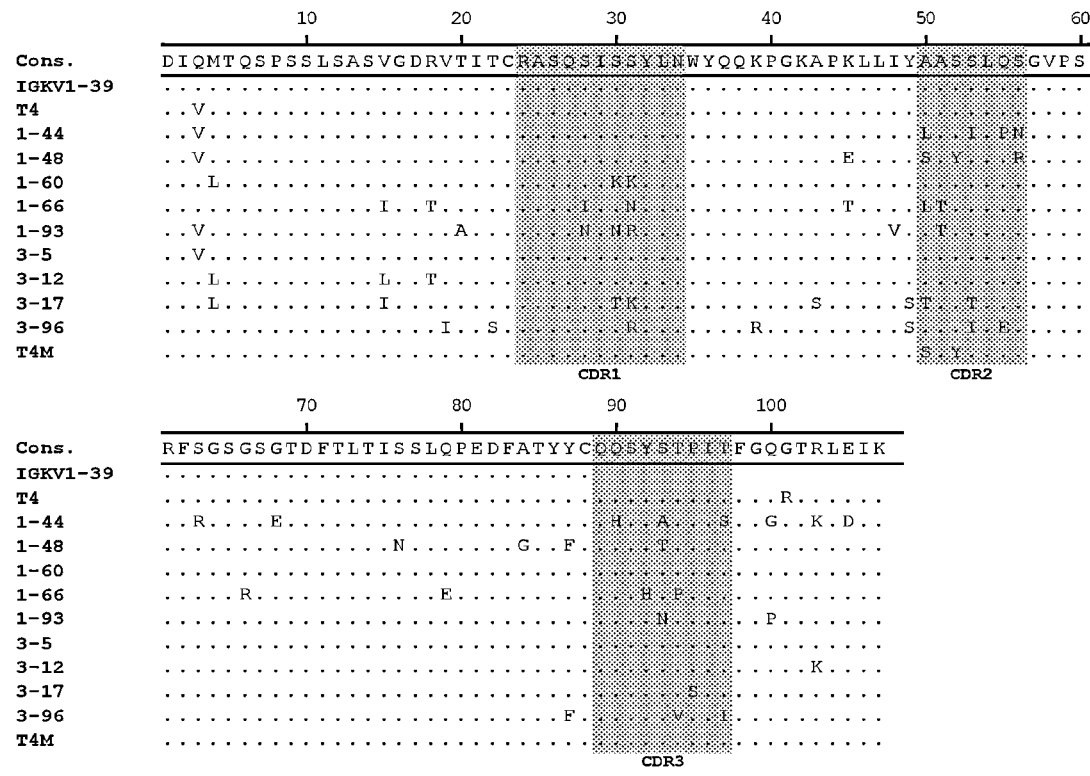
FIG. 6 shows an alignment of the amino acid sequence of VLs of T4-derived variant Abs and the germline sequence. Dots denote positions having identical amino acids. The amino acid numbering is based on the consensus sequence. CDRs are determined according to the Kabat system and are shaded in grey.

Further sequence analysis suggested that S50 and Y52 in the Vk's CDR2 of 1-48 Ab contributed to the improved affinity of 1-48 Ab (FIG. 6).

Figure 7:
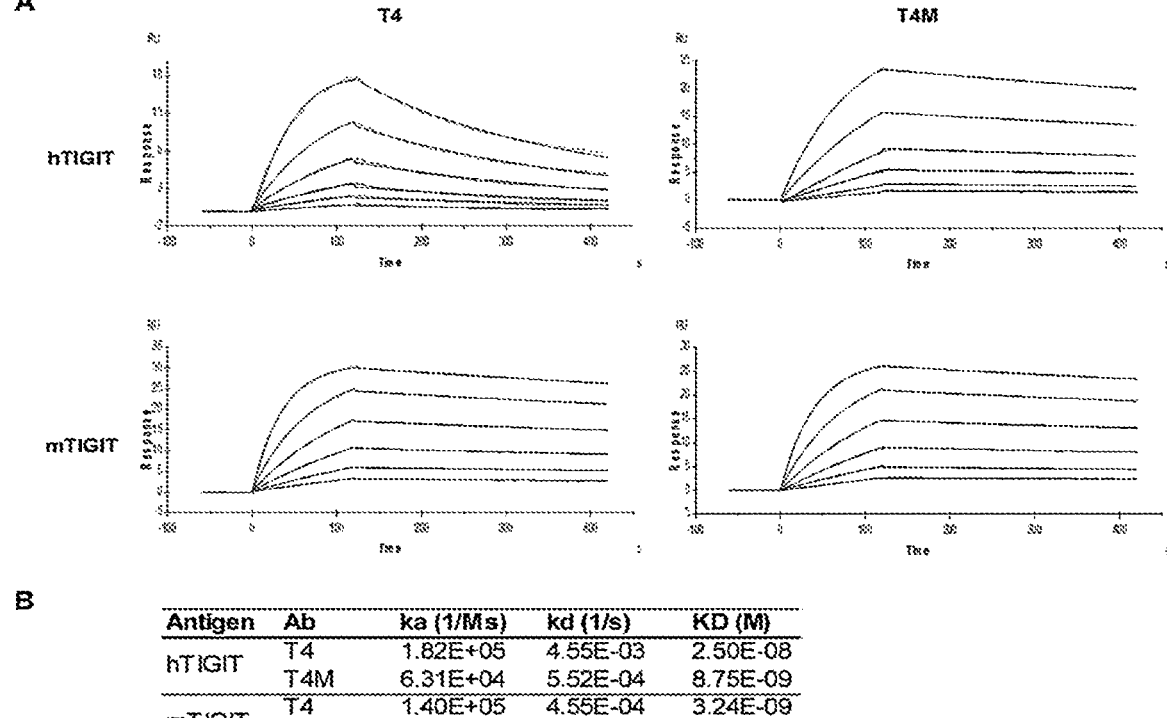
FIGS. 7A-B show the binding kinetics of T4 and T4M Abs to hTIGIT and mTIGIT using SPR. A) Multi-cycle kinetic analyses of the interactions between anti-TIGIT Abs and hTIGIT or mTIGIT using Biacore T200. B) A table listing the values of ka, kd, and KD.

Building on this result, an antibody, T4M, was generated to incorporate these two amino acids (S50 and Y52) into the germline Vk sequence of T4. The analysis of binding kinetics confirmed that the variant T4M had improved binding affinity as compared to the parental T4 Ab, especially to hTIGIT (FIG. 7).

Example 3. Improving Binding Affinity of hm7 by VL-Chain Shuffling

To further improve hm7 binding affinity, the present inventors made a VL chain shuffled phage display library, in which VH of hm7 was fixed and paired with a library of different Vl (lambda variable light chain) chains. The final library (hm7VH/Vl lib) being constructed had a size of about $1 \times 10^8$.

Figure 8:
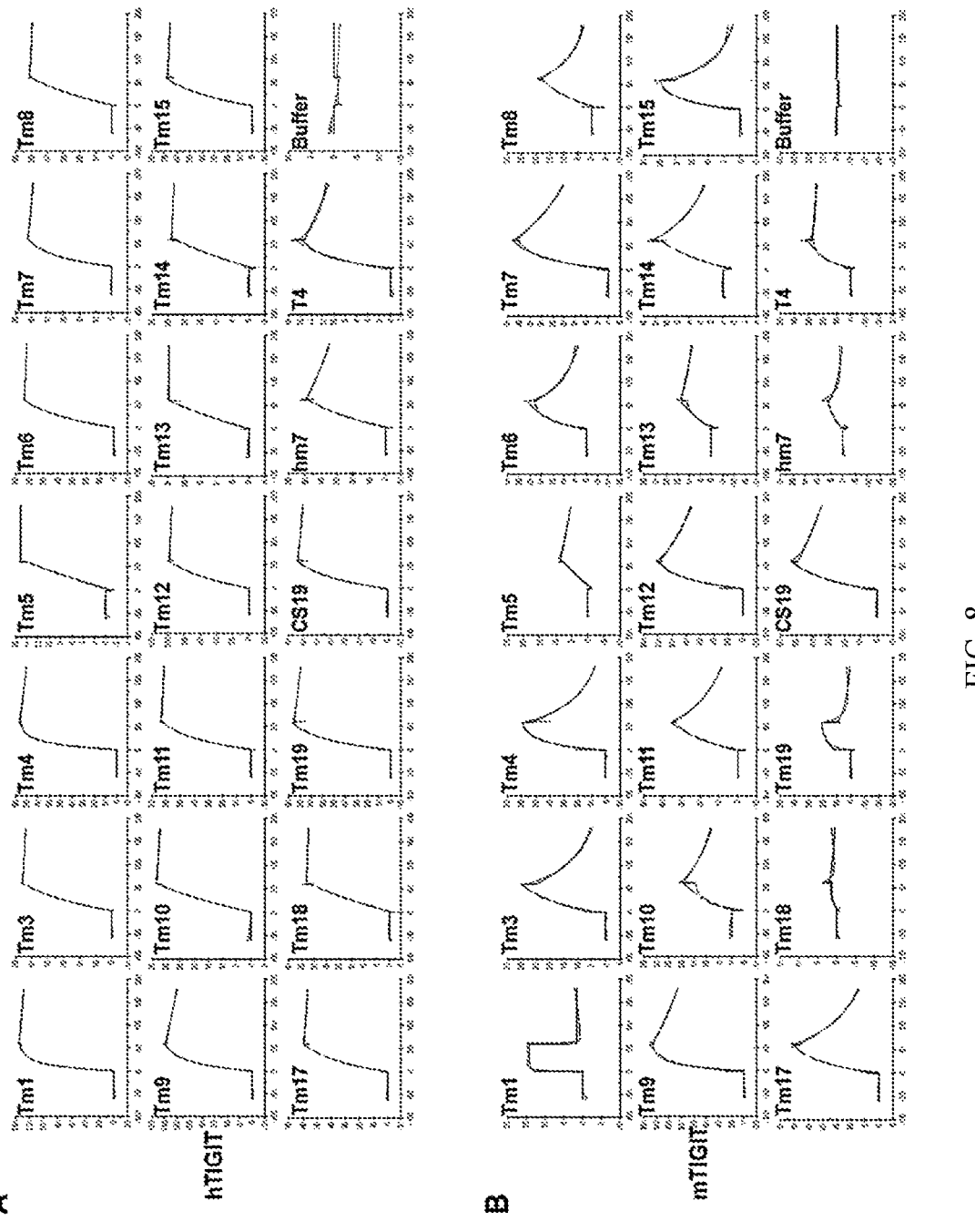
FIGS. 8A-B show the binding kinetics of anti-TIGIT Abs (hm7-derirved Abs, hm7 and T4) to hTIGIT (A) or mTIGIT (B) using SPR.

By using hTIGIT captured on streptavidin-conjugated magnetic M-280 Dynabeads® (Life Technologies) as target, the hm7VH/Vl lib was screened for two rounds. 576 clones were screened for binding with hTIGIT by ELISA. Most clones were positive and were picked for sequencing. 47 Abs were converted into full-length hIgG1 and tested for binding to hTIGIT or mTIGIT using SPR. 18 clones, Tm1, Tm3, Tm4, Tm5, Tm6, Tm7, Tm8, Tm9, Tm10, Tm11, Tm12, Tm13, Tm14, Tm15, Tm17, Tm18, Tm19, and CS19 with different Vl chain sequences showed higher affinity than the parental Ab hm7 for binding to hTIGIT (FIG. 8). Among them, CS19 showed the strongest binding activity to both hTIGIT and mTIGIT than other Abs.

CS19 was further engineered to minimize the potential undesired post-translational modifications and immunogenicity. Two new Vls derived from CS19 Ab were generated and named as CS19ME-Vl (CS19-Vl-Q108K/M49L/N97E) and CS19ME-N-Vl (CS19-Vl-Q108K/M49L/N97E/K55N), respectively (FIG. 9).

Figure 10:
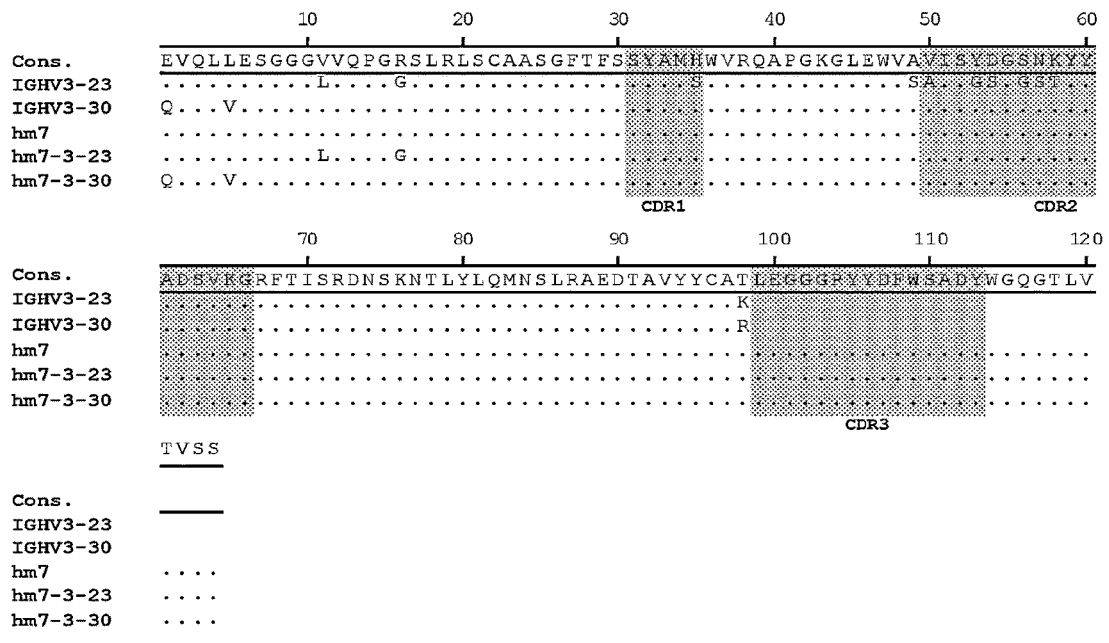
FIG. 10 shows the amino acid sequence alignment of the VH of variants derived from hm7 Ab. Dots denote positions having identical amino acids. The amino acid numbering is based on the consensus sequence. CDRs are determined according to the Kabat system and shaded in grey.

For the VH of hm7 antibody, two new VHs were constructed on the basis of germline analysis and named as hm7-3-23-VH (hm7-VH-V11L/R16G) and hm7-3-30-VH (hm7-VH-E1Q/L5V), respectively (FIG. 10).

Figure 11:
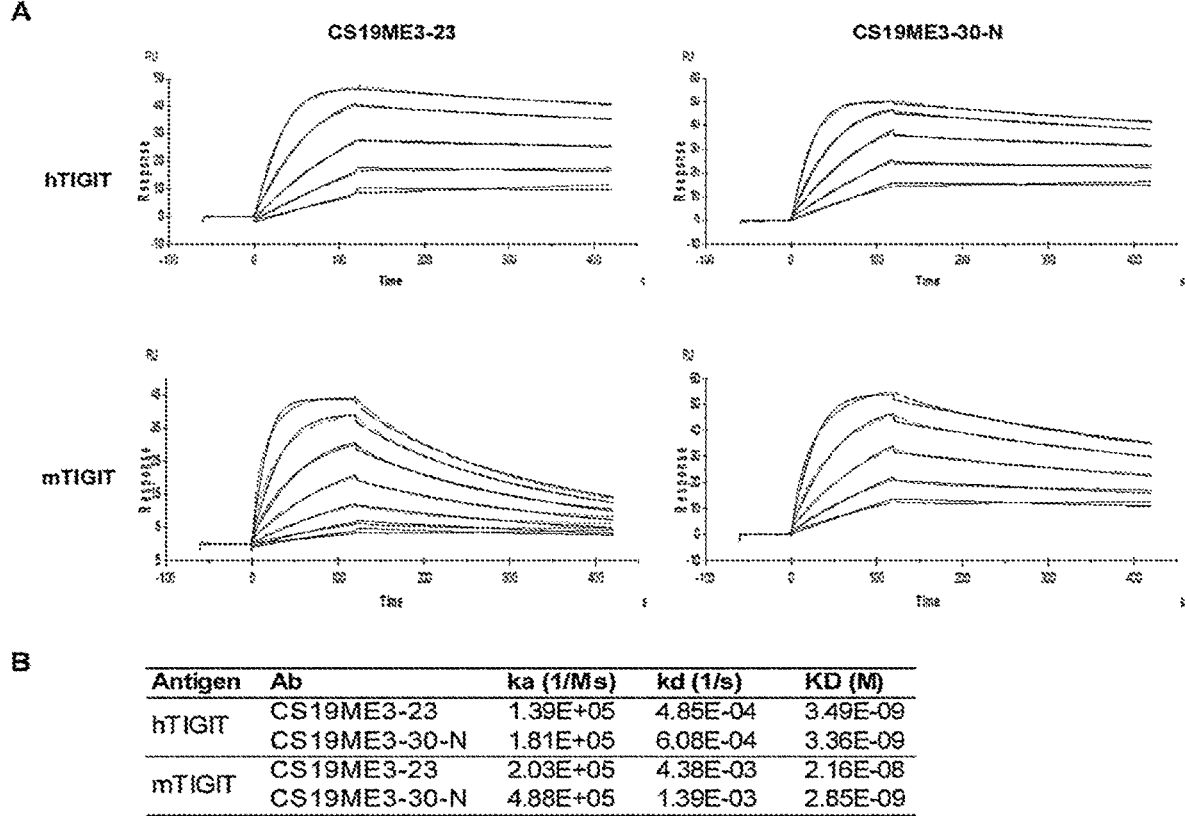
FIGS. 11A-B show the binding kinetics of the anti-TIGIT Abs to hTIGIT or mTIGIT using SPR. A) Multi-cycle kinetic analyses of the interactions between anti-TIGIT Abs and hTIGIT or mTIGIT using T200.B) A table listing the values of ka, kd, and KD.

Combining the above-mentioned VHs and VLs, two new antibodies, CS19ME3-23 (heavy chain: hm7-3-23-VH; light chain: CS19ME-Vl) and CS19ME3-30-N Ab (heavy chain: hm7-3-30-VH; light chain: CS19ME-N-Vl) were generated. Both of them showed increased binding affinity as compared to their parental hm7 Ab (FIG. 11).

Figure 9:
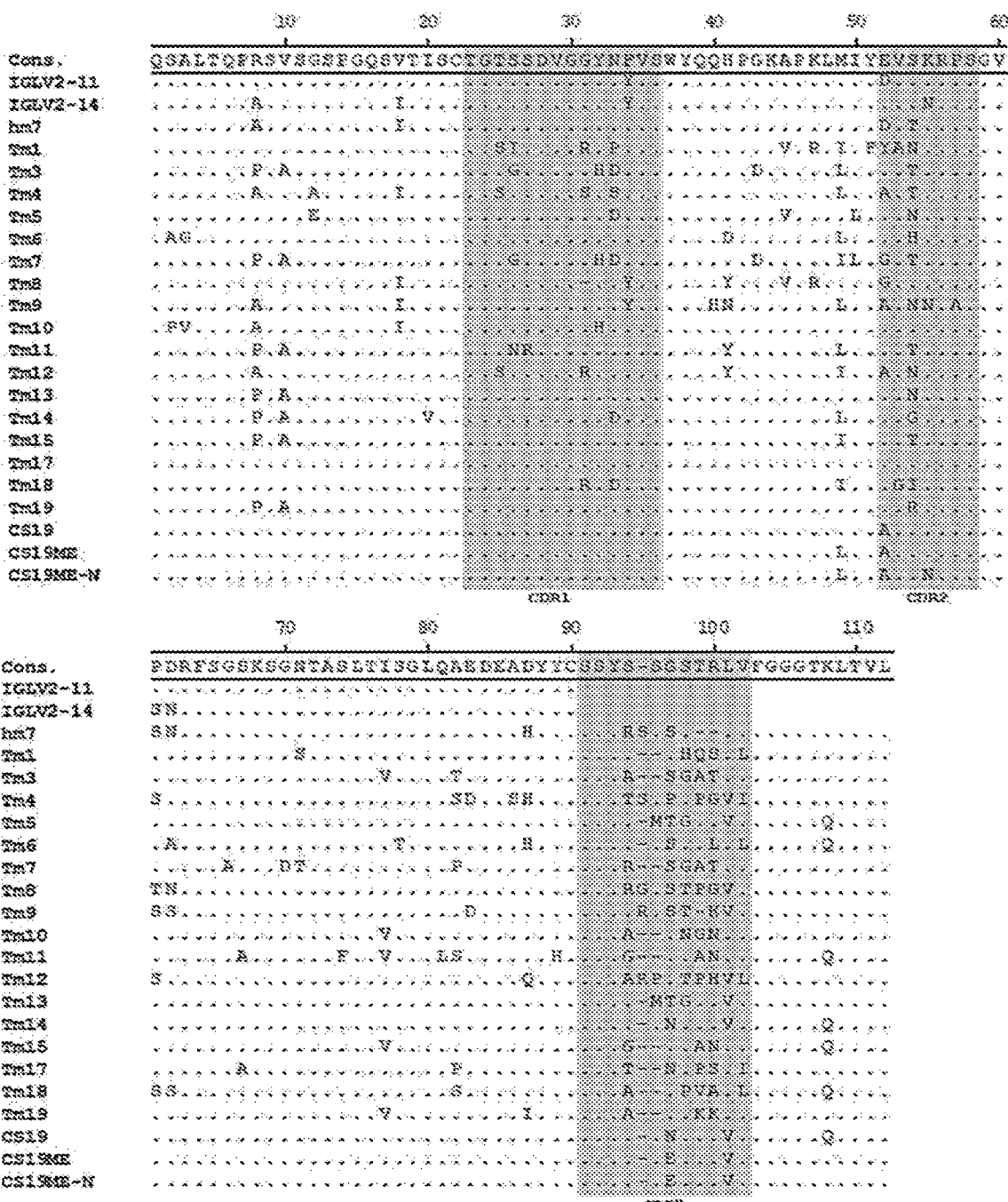
FIG. 9 shows the amino acid sequence alignment of the VL of variants derived from hm7 Ab. Dots denote positions having identical amino acids. The amino acid numbering is based on the consensus sequence. CDRs are determined according to the Kabat system and shaded in grey.

The VH and VL sequences of hm7 and hm7-derived clones are listed in FIG. 10 and FIG. 9, respectively. As shown in FIG. 9, the light chain CDR1, CDR2 and CDR3 (LCDR1, LCDR2 and LCDR3) are amino acids 23-34, amino acids 52-58 and amino acids 91-102, respectively, in the amino acid sequence of respective VL according to a Kabat system. As shown in FIG. 10, the heavy chain CDR1, CDR2 and CDR3 (HCDR1, HCDR2 and HCDR3) are amino acids 31-35, amino acids 50-66 and amino acids 99-113, respectively, in the amino acid sequence of respective VL according to a Kabat system.

TABLE 2

| Sequence information of CS19ME3-23 and CS19ME3-30-N | | | | |
|---|---|---|---|---|
| Ab | VH nucleotide SEQ ID NO. | VH amino acid SEQ ID NO. | VH nucleotide SEQ ID NO. | VH amino acid SEQ ID NO. |
| CS19ME3-23 | 29 | 27 | 28 | 26 |
| CS19ME3-30-N | 36 | 34 | 35 | 33 |

Example 4. Epitope Mapping of the Anti-TIGIT Antibodies

Figure 12:
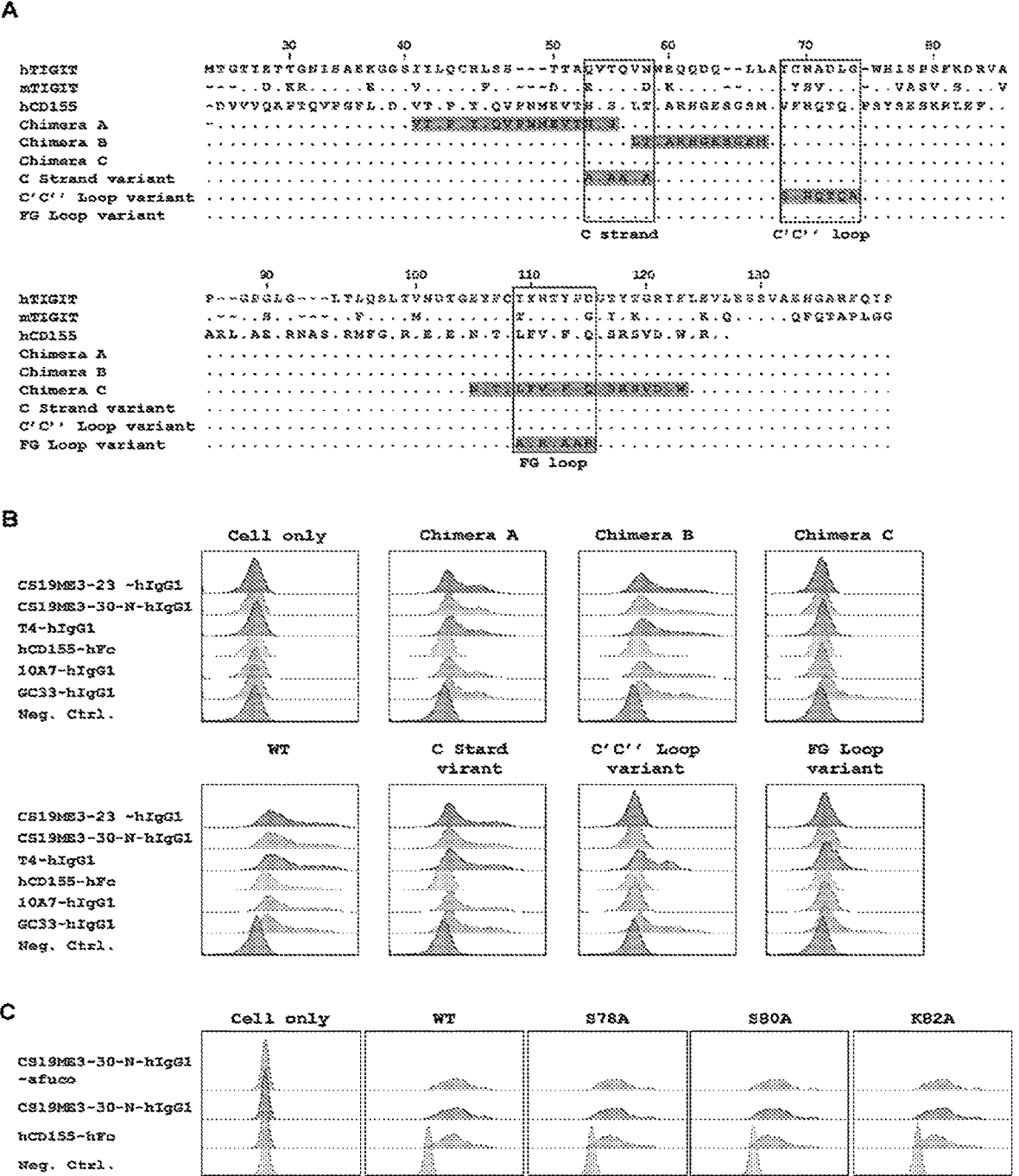
FIGS. 12A-C show the epitope mapping of the anti-TIGIT Abs. A) Amino acid sequence alignment of N-terminal IgV domains of hTIGIT, mTIGIT, hCD155, three hTIGIT/hCD155 chimeras, and three hTIGIT variants. Dots denote positions having identical amino acids, and dashes indicate gaps. The replaced or mutated regions are shaded with grey color. The amino acid numbering is based on hTIGIT. B) Flow cytometry analysis of different Abs or hCD155-hFc ligand binding to CHO cells transiently expressing full-length hTIGIT (wild type, WT), or its chimeras or variants. The secondary Ab staining only was used as a negative control (Neg. Ctrl.). The cell surface expression levels of WT hTIGIT, chimeras, and variants were assessed by using a mAb (GC33) recognizing the N-terminal tag. C) Flow cytometry analysis of different Abs or hCD155-hFc ligand binding to 293T cells transiently expressing full-length hTIGIT (wild type, WT), or its three variants (S78A, S80A, K82A). The secondary Ab staining only was used as a negative control (Neg. Ctrl.). The cell surface expression levels of WT hTIGIT and variants were assessed by using hCD155-hFc.

For epitope mapping, chimeras of human TIGIT IgV domain and N-terminal IgV domain D1 of hCD155 were constructed by replacing residues in the extracellular regions of hTIGIT with the corresponding residues from hCD155 D 1. Three hTIGIT variants and three chimeras were generated as shown in FIG. 12A-C. These chimera and variants were expressed by transient transfection of CHO or 293T cells, their cell surface expression levels were assessed by using a mAb GC33 recognizing the N-terminal tag fused to each of the chimera and variant or hCD155-hFc (4). The binding of testing Abs in human IgG1 (hIgG1) format or hCD155-hFc to these transfectants were detected by using goat anti-human IgG-FITC antibody (Thermo Fisher Scientific). The cells were then analyzed with FACS machine (BD Accuri™ C6).

By transfecting CHO cells with these hTIGIT/hCD155 chimeras or hTIGIT variants, and by subsequently analyzing T4, CS19ME3-23, and CS19ME3-30-N Abs binding to these CHO transfectant cells by FACS, it was identified that the FG Loop in the extracellular IgV domain of hTIGIT is critical for these Abs' binding (FIG. 12B). It was found that the FG Loop is also important for binding to the hCD155 ligand, which is consistent with previous findings (5). Thus, by binding to the FG Loop, these three Abs block the binding of TIGIT to its ligand CD155. Due to the high amino acid sequence homology in this loop between hTIGIT and mTIGIT, these three Abs are able to cross-react with both of them. That is, T4, CS19ME3-23, and CS19ME3-30-NAbs possess cross-species reactivity to human and mouse TIGIT.

In addition, based on the epitope mapping result, the C-C' loop also involves in the binding of CS19ME3-23 and CS19ME3-30-N to TIGIT.

US2018/0186875A1 (Genentech) showed that amino acid residues S78, S80, and K82 of human TIGIT are key epitopic residues for their anti-TIGIT antibodies. To investigate the role of these residues in the binding of anti-TIGIT antibodies of the present disclosure to hTIGIT, three hTIGIT variants each having a single point mutation selected from S78A, 580A, and K82A were generated. By transfecting 293T cells with these hTIGIT variants and by subsequently analyzing CS19ME3-30-N Abs binding to these 293T transfectant cells by FACS, it was identified that none of the three residues in the extracellular IgV domain of hTIGIT is critical for these Abs' binding (FIG. 12C).

Example 5. Anti-TIGIT Antibodies Exert Effective Ligand Blocking Function in ELISA The ELISA-based competition assays were performed in a manner similar with ELISA-based binding assays, except that the tested Abs were incubated with captured antigens in the presence of competitive ligands. Briefly, different human IgG1 antibodies at serially diluted concentrations were mixed with 0.05 µg/mL of the extracellular domain of hCD155 fused with mouse Fc tag (hCD155-mFc), 0.8 µg/mL of the extracellular domain of mCD155 fused with mouse Fc tag (mCD155-mFc), or 5 µg/mL of the extracellular domain of hCD112 fused with mouse Fc tag (hCD112-mFc), and added to the ELISA plates to compete for the binding between TIGIT and CD155. The signal was measured via ligand detection using HRP-anti-mouse IgG secondary Ab (Thermo Fisher Scientific).

Figure 13:
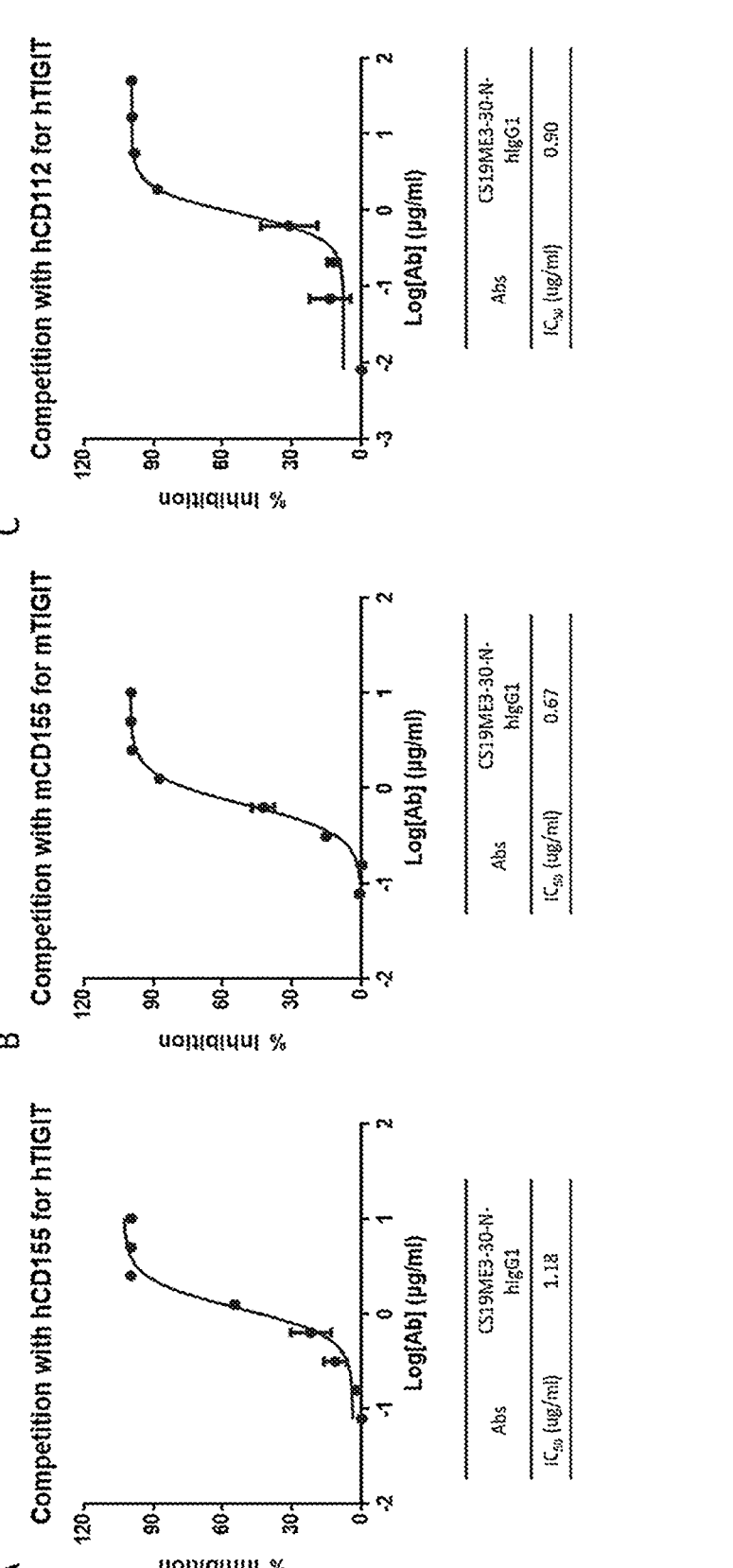
FIGS. 13A-C show the Ligand competition activities of anti-TIGIT Ab analyzed by ELISA. CS19ME3-30-N Ab in IgG1 form at serially diluted concentrations was tested for competing of the binding of hCD155-mFc (A), mCD155-mFc (B), or hCD112 (C) to biotinylated hTIGIT, mTIGIT, or hTIGIT captured by immobilized streptavidin on an ELISA plate.

CD155 (also known as PVR or Nec1-5) and CD112 (also known as Pvr12 or Nectin-2) are two major ligands that are heavily expressed on many cancer cells (6). They both interact with TIGIT to inhibit T/NK cell functions (6). The competitive activity of anti-hTIGIT Ab for TIGIT binding has been confirmed. The results showed that anti-hTIGIT Ab showed competitive activity for TIGIT with its ligands CD155 or CD112 in ELISA assay (FIGS. 13A-C).

Example 6. Anti-TIGIT Antibodies Exert Effective Ligand Blocking Function in Cell-Based Assays In this example, the NK cell cytotoxicity assay conducted by the inventors is described to show the ligand blocking function of the anti-TIGIT antibodies of the present application.
1) Establishment of Stable Cell Lines
Previous studies showed that YTS cells (an NK cell line) achieve restricted killing of 721.221 target cells (a MHC class I-negative human B cell line) (6-8) and showed that this killing can be effectively inhibited by expressing hTIGIT in YTS cells and by expressing hCD155 in 721.221 cells (6, 7).

Figures 14, 15:
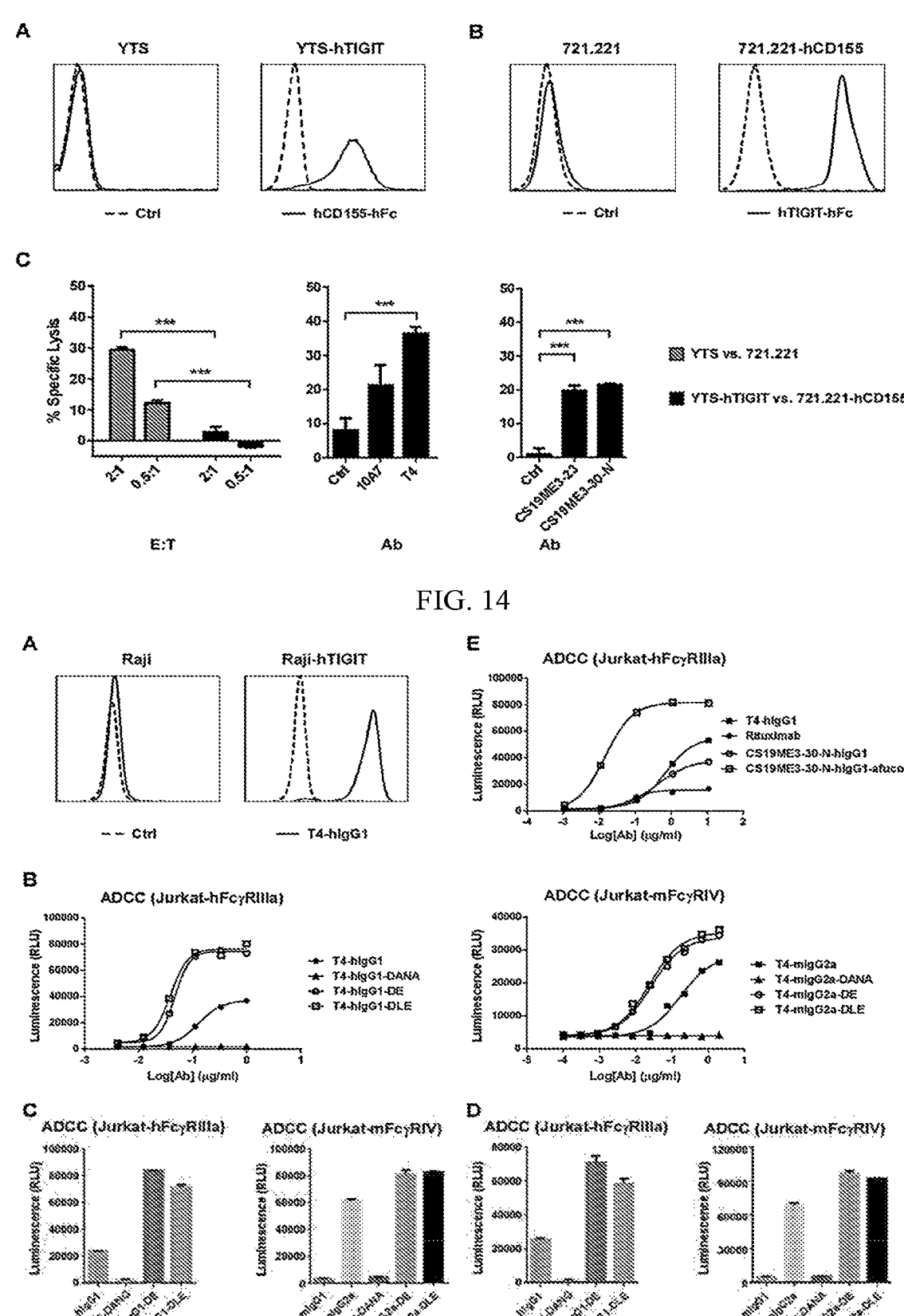
FIGS. 14A-C show the anti-TIGIT Abs effectively reverse NK cell cytotoxicity suppressed by TIGIT-CD155 interaction. A-B) The expression of hTIGIT on YTS-hTIGIT or hCD155 on 721.221-hCD155 stable cell line was assessed using anti-TIGIT Ab (10A7) or hTIGIT-Fc fusion protein by flow cytometry. C) TIGIT/CD155 engagement disrupted cytotoxicity of YTS cells (Left) and T4, CS19ME3-23, and CS19ME3-30-N Abs effectively reversed NK cell cytotoxicity suppressed by TIGIT-CD155 interaction (Middle and Right). For killing assays of 721.221 target cells by NK effector YTS cells, and killing of 721.221-hCD155 cells by YTS-hTIGIT cells, the effector-to-target (E:T) ratios are indicated on the x axis. For killing assays in the presence of Abs, the E:T ratio was 2:1. The antibody 10A7 was included as an anti-TIGIT reference Ab control. Abs were full-length hIgG1 Abs.
FIGS. 15A-E show the ADCC effector functions induced by the anti-TIGIT Abs of the present application. A) Raji-hTIGIT cell lines were generated for Fc-mediated effector functional analysis in vitro. The expression of hTIGIT on Raji WT and Raji-hTIGIT cells were analyzed by FACS. B) ADCC effector function induced by T4 Abs. ADCC activity was measured using a reporter assay system. Jurkat-NFAT-Luc2p/mFcγRIV (Jurkat-mFcγRIV) or Jurkat-NFAT-Luc2p/ hFcγRIII (Jurkat-hFcγRIII) was used as effector cells, and Raji-hTIGIT cells were used as target cells, respectively. Abs were tested at the indicated concentrations with three replicates. The E:T ratio was 6:1. C-D) ADCC effector function induced by CS19ME3-23 (C), or CS19ME3-30-N (D) in hIgG or mIgG formats. ADCC function was detected according to the method described in panel B in medium containing 0.1 µg/ml Abs. E) ADCC effector function induced by hIgG and afucosylated hIgG1 variants. Detection method was same as the method described in panel B.

The present inventors established YTS cells stably expressing hTIGIT (YTS-hTIGIT) and 721.221 cells stably expressing hCD155 (721.221-hCD155) (FIG. 14A-B). For the generation of the stable cell lines, the full-length cDNA of hTIGIT or hCD155 was amplified by PCR and cloned into a mammalian cell expression plasmid. YTS cells or 721.221 cells were transfected with corresponding plasmids using the Neon transfection system (Thermo Fisher Scientific) or Nucleofector transfection system (Lonza, Nucleofector kit V) following the manufacture's instruction, respectively. 48 hrs after transfection, the transfected cells were immunostained with hCD155-hFc or hTIGIT-hFc, respectively, and positive cells were sorted. The positive cells identified by sorting were cultured under the selection of G418.
2) Cell Cytotoxicity Assay
721.221-hCD155 cells (5000 cells/well) were incubated with YTS-hTIGIT at the various E:T (effector-to-target) in the presence of 5 µg/well Abs for 6 hours. Then lactate dehydrogenase (LDH) release by cells was detected by following the instructions of a CytoTox 96® Non-Radioactive Cytotoxicity Assay kit (Promega). Cytotoxicity percentages were calculated by following the manufacturer's instruction.

As a result, it was confirmed that the interaction of hTIGIT expressed on YTS and hCD155 expressed on 721.221 inhibited the killing of their parental cells (YTS to 721.221) effectively (FIG. 14C-left panel).
3) Ligand blocking Functional Assay
To test the effect of the anti-TIGIT antibodies of the present application, the above-mentioned NK cell cytotoxicity assay was performed in the presence of the antibodies T4, CS19ME3-23, and CS19ME3-30-N. It was found that T4, CS19ME3-23, and CS19ME3-30-N Abs restored the ability of YTS-hTIGIT cells to kill 721.221-hCD155 cells (FIG. 14C-middle and right), thus demonstrating that these Abs efficiently blocks TIGIT-CD155-interaction-mediated inhibitory functions.

Example 7. Anti-TIGIT Antibodies of the Present Application Induced Fc-Mediated Effector Functions in Vitro

Construction of Chimeric Abs in the Context of Different Fc

Various chimeric antibodies were constructed in the context of different human and murine IgG isotypes (hIgG1, mIgG1, and mIgG2a), and three Fc variants of hIgG1 and mIgG2a isotypes: an Fc-D265A/N297A (DANA) or D265A/N297G (DANG) variant with abolished FcγR-mediated effector functions (9-13); Fc-S239D/I332E (DE) variant, Fc-S239D/A330L/I332E (DLE) variant, and afucosylated hIgG1 (expressed by FUT8 knockout 293F cells or CHO cells) with enhanced FcγR-mediated effector functions (14-22).

ADCC Assay Using NK Cell Lines

For ADCC assays, a Raji cell line stably expressing full-length hTIGIT (Raji-hTIGIT) was established and used as target cells in this assay. A Jurkat cell line stably expressing FcγR (hFcγRIIIa (F158) or mFcγRIV receptor) and a nuclear factor of activated T cells (NFAT)-response-element driven firefly luciferase reporter (named as Jurkat-NFAT-Luc2p/hFcγRIIIa (F158) or Jurkat-NFAT-Luc2p/mFcγRIV) was generated and used as effector cells.

Target cells (15000 cells/well) were seeded into the wells of U-bottom 96-well cell culture plates and incubated briefly with various concentrations of different Abs. The effector cells were then added (90000 cells/well) into the wells containing the target cells and the Abs at various concentrations in RPMI 1640 medium supplemented with 1% heat-inactivated fetal bovine serum, and incubated for 5 hours at 37° C. ADCC activity was determined by the luciferase expression according to the instructions of Bright-Glo™ Luciferase assay reagents (Promega).

ADCP Assay Using Mouse Macrophages

For ADCP assays, mouse bone marrow-derived macrophages (BMDMs) were used as effector cells in this assay. To prepare BMDMs, mouse bone marrow cells were collected from the tibia and femurs of C57 mice, and induced by Granulocyte-macrophage colony stimulating factor (GM-CSF) in L929 supernatants for 3 days. The Raji-hTIGIT stable cell line was labeled with CF SE and used as target cells. The BMDMs were labeled with anti-mouse F4/80-Alex Fluor647 (Thermo Fisher Scientific) prior to incubation with target cells. The CF SE labeled target cells were plated at a density of $2 \times 10^5$ cells/well and incubated with different antibodies of the present application (20 μg/ml) at RT for 15 mins, and then added to the labeled BMDMs ($1 \times 10^5$ cells/well, resulting in a E:T ratio of 1:2) at 37° C. for 2 hours in 5% $CO_2$ humidified incubator in DMEM+10% heat-inactivated FBS medium. Phagocytosis of CF SE-labeled target cells by anti-mouse F4/80 Ab-labeled macrophages was recorded using a Nikon MR Confocal Microscope.

Complement-Mediated Cytotoxicity (CDC) Assay

For CDC assays, the Raji-hTIGIT stable cells were used as target cells, and seeded in a 96-well U-bottom plate at $4 \times 10^5$ cells/well, incubated with 100 nM anti-TIGIT antibodies of the present application at indicated concentrations in the presence of 5% rabbit sera (Sigma). After 2 hours of incubation, the supernatants in each well were analyzed for LDH release using a CytoTox 96® Non-Radioactive Cytotoxicity Assay kit (Promega).

Seeking how anti-TIGIT Abs exert their anti-tumor effects independent of the interaction between TIGIT and CD155 on tumors, the present inventors first examined if anti-TIGIT Abs possess Fc-mediated effector functions using in vitro assays, including ADCC, ADCP, and CDC.

Previous studies showed that mouse FcγRIV was the predominant receptor involved in ADCC in mice and it was proposed to be a 'functional' homolog of human FcγRIIIa (23, 24). To test Abs' ADCC, the present inventors established reporter systems in which Jurkat T lymphocyte cells expressing the hFcγRIIIa (F158 allele) or mFcγRIV (23, 24) and an NFAT response element driving expression of firefly luciferase were used as effector cells; and in which Raji cells stably expressing hTIGIT (Raji-hTIGIT) were used as target cells. For testing mouse IgG Abs' ADCC, the present inventors used a modified system (25) in which Jurkat T lymphocyte cells expressing the mouse FcγRIV and an NFAT response element driving expression of firefly luciferase (Jurkat-NFAT-Luc2p/mFcγRIV) were used as effector cells, and Raji-hTIGIT were used as target cells. While, for testing hIgG Abs' ADCC, the present inventors used a system (25)

in which human Jurkat T lymphocyte cells expressing the FcγRIIIa (F158 allele) and an NFAT response element driving expression of firefly luciferase (Jurkat-NFAT-Luc2p/hFcγRIIIa) were used as effector cells, and Raji-hTIGIT were used as target cells (FIG. 15A). This ADCC assay revealed that T4, CS19ME3-23, and CS19ME3-30-N, either in hIgG1 or mIgG2a isoform, induced cytotoxic effect executed by the effector cells against the target cells. As expected, hIgG1/mIgG2a-DE, hIgG1/mIgG2a-DLE, and hIgG1-afucosylated variants exhibited significantly higher ADCC activities than wild type hIgG1 and mIgG2a; whereas hIgG1/mIgG2a-DANA/DANG and mIgG1 did not induce any ADCC function (FIG. 15B-E).

Figures 16, 17:
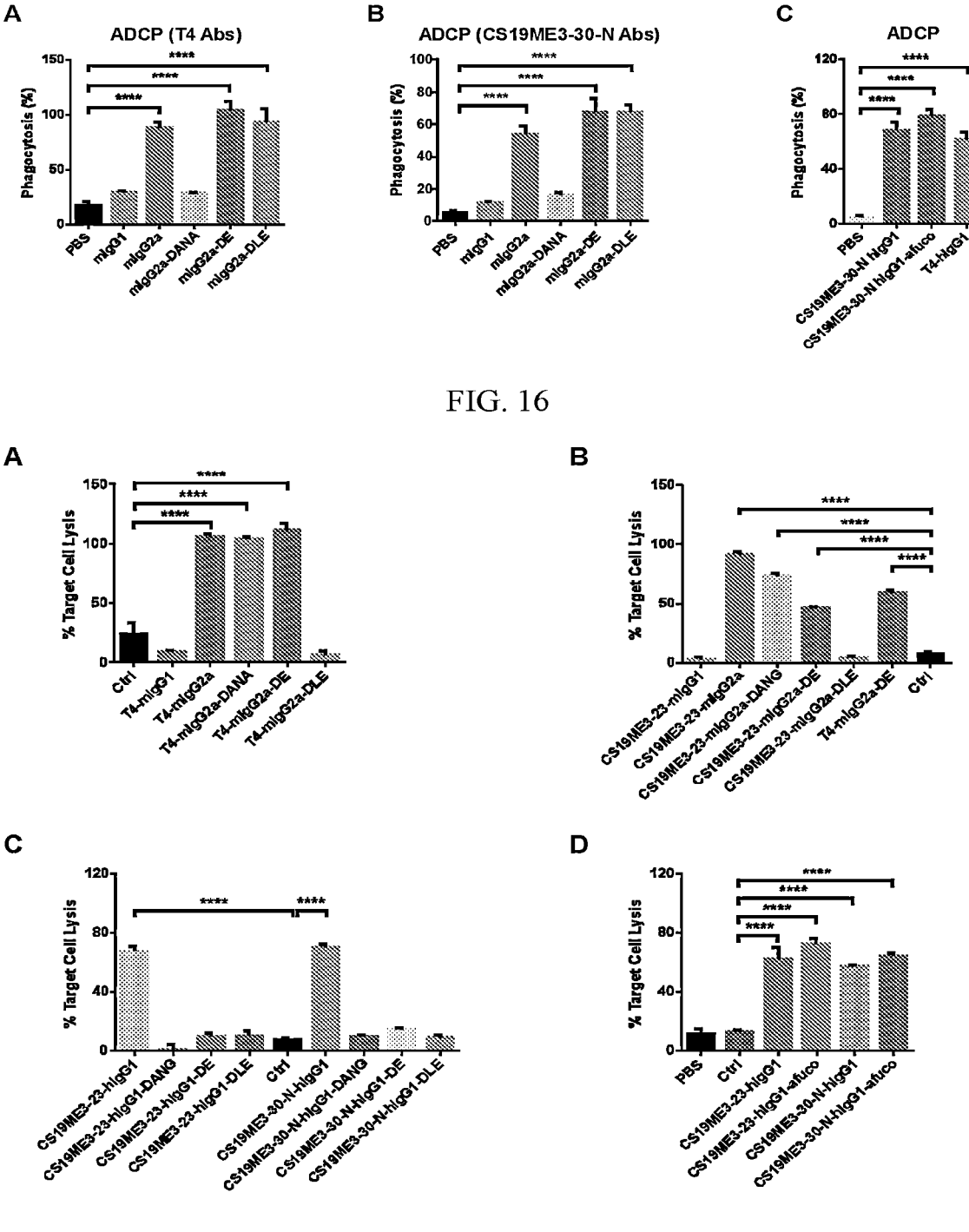

For testing Abs' ADCP activity, BMDMs and Raji-hTIGIT were used as effector and target cells, respectively. T4 and CS19ME3-30-N Abs in the context of mIgG2a isotype, mIgG2a-DE variant, mIgG2a-DLE variant, and hIgG1 isotype exhibited similar levels of ADCP activities, whereas mIgG1 and mIgG2a-DANA/DANG did not induce ADCP (FIG. 16).

For testing Abs' CDC activity, Raji-hTIGIT cell line was used as target cells and lactate dehydrogenase (LDH) release was used as readout of target cell lysis through complements. For mIgG Abs, T4-mIgG2a, T4-mIgG2a-DE, and T4-mIgG2a-DANA showed similar CDC activities, while T4-mIgG1 and T4-mIgG2a-DLE did not elicit CDC at all (FIG. 17A). CS19ME3-23-mIgG2a showed stronger CDC than CS19ME3-23-mIgG2a-DANG, and CS19ME3-23-mIgG2a-DANG showed stronger CDC than CS19ME3-23-mIgG2a-DE, while CS19ME3-23-mIgG1 and CS19ME3-23-mIgG2a-DLE did not elicit CDC at all (FIG. 17B). For CS19ME3-23 and CS19ME3-30-N hIgG Abs, only hIgG1 showed effective CDC function, but not other variants (FIG. 17C). Additionally, their hIgG1-afucosylated variants exhibited similar CDC activities as hIgG1 (FIG. 17D).

Collectively, these studies demonstrated that anti-TIGIT antibodies of the present application possess Fc-mediated effector functions in vitro, in addition to its activity in blocking TIGIT binding to CD155. These Ab Fc variants provided a tool set for the subsequent in vivo studies using mouse models.

Example 8. Anti-TIGIT Antibodies of the Present Application Exerted Potent Anti-Tumor Activities Depending on Fc-Mediated Effector Functions in Animal Models In this example, the anti-tumor effects of the anti-TIGIT Abs were evaluated using immune-competent murine syngeneic tumor models. The effector functions of the anti-TIGIT Abs were also examined for their contributions to the anti-tumor effects.

Detection of mCD155 Expression on Mouse Tumor Cell Lines Using FACS

Figure 18:
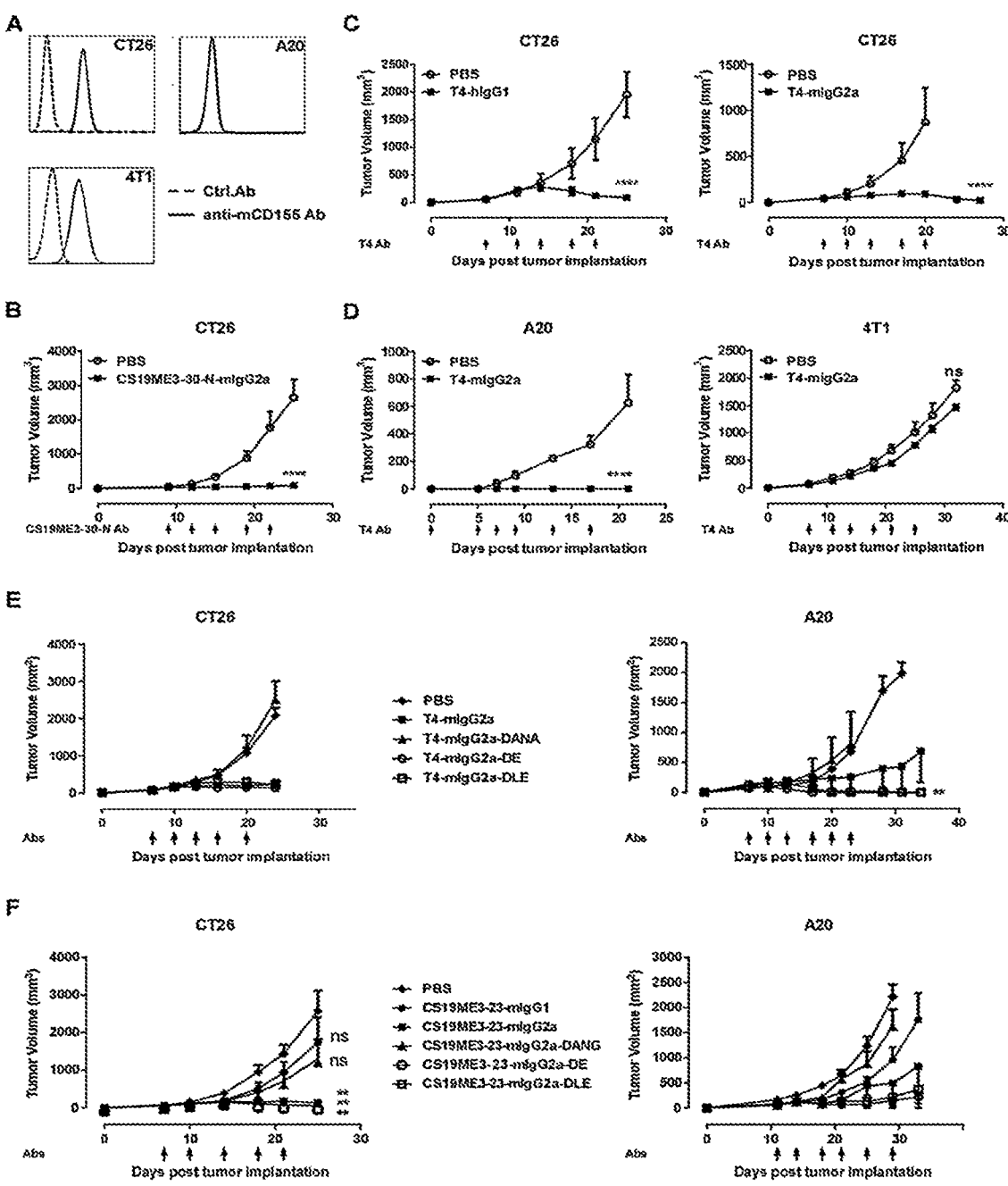
Figure 19:
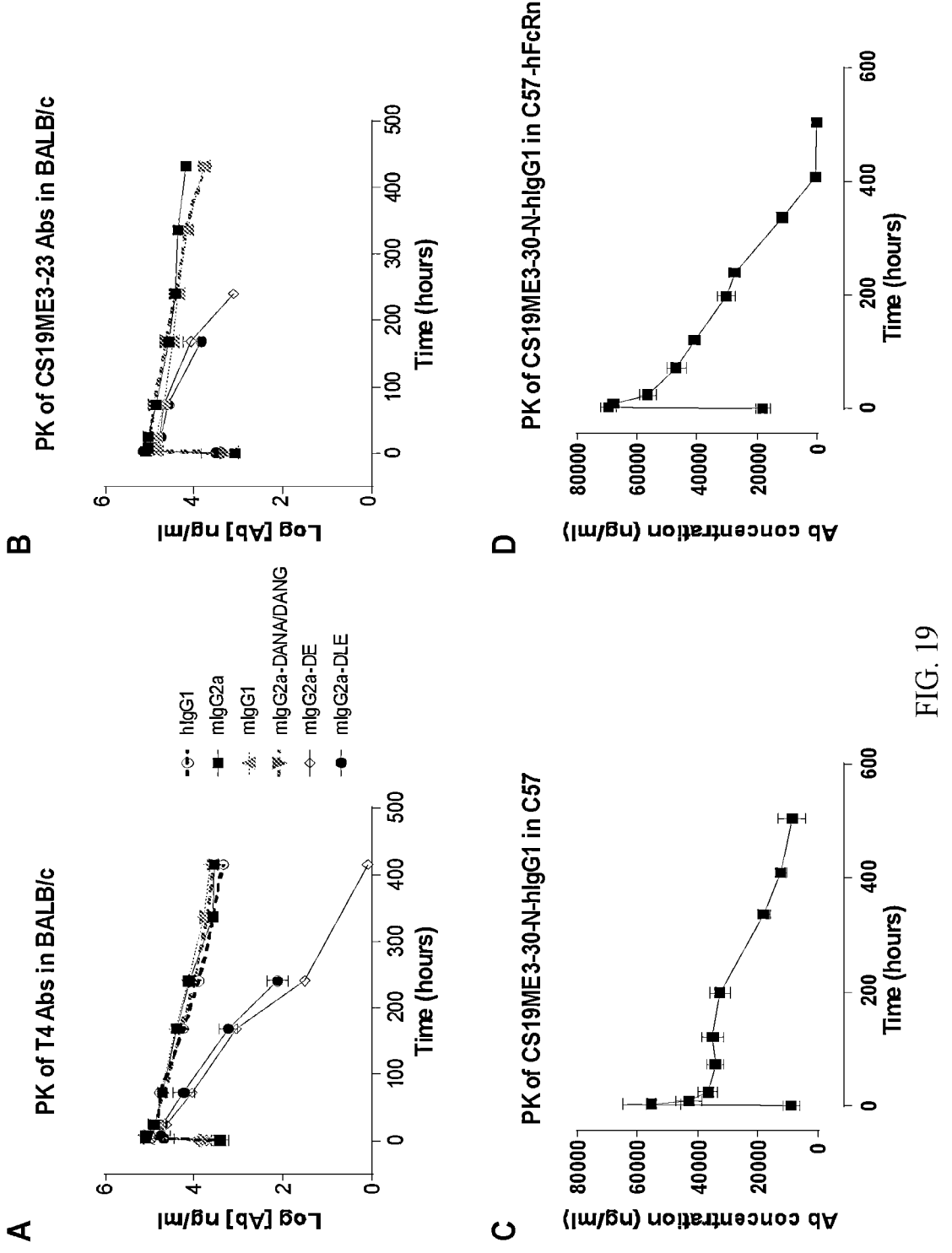

Murine tumor cell lines, CT26 (colon carcinoma), A20 (B cell lymphoma) and 4T1 (breast cancer) were examined for the expression of mouse CD155 (mCD155). A rat anti-mCD155 Ab 4.24.1 (Biolegend) was used for examining the mCD155 expression on the tumor cell surface. Donkey anti-Rat IgG-Alexa Fluor 488 antibody was used as a secondary Ab (Thermo Fisher Scientific). For staining A20 cells, the cell surface Fc receptors were pre-blocked using 2.4G2 (an antibody blocking Fc binding to murine FcγRII and FcγRIII) prior to mCD155 staining (FIG. 18A).

Animal Studies

All animal experiments were conducted following the National Guidelines for Housing and Care of Laboratory Animals in China and performed under the approved IACUC protocols at National Institute of Biological Sciences, Beijing.

For establishing mouse tumor models, 6-8 weeks old female BALB/c mice were inoculated subcutaneously with $1\text{-}3 \times 10^5$ CT26, A20, or 4T1 cells in the right flank. Based on similar mean tumor volumes (50-100 $mm^3$ except as otherwise specifically indicated), mice were randomized into groups (n=3-6/group) and received intraperitoneal injection of anti-TIGIT Abs (10 mg/kg), its variants, or PBS buffer two times per week for a total of 5 or 6 injections. Tumor volume was measured with an electronic caliper and calculated using the modified ellipsoid formula as 1/2×(length× width).

For both CT26 and A20 tumor models, treatment with CS19ME3-30-N-mIgG2a, T4-hIgG1, T4-mIgG2a, or CS19ME3-23-mIgG2a significantly inhibited tumor growth and even induced tumor regression as compared to the control group (FIG. 18B-E).

To test if the effector functions of these anti-TIGIT Abs contribute to their anti-tumor effect in vivo, the present inventors compared the anti-tumor activities of the set of Fc variants of the Abs with either enhanced or abolished effector functions. In BALB/c mice bearing CT26 or A20 tumor models, treatment with anti-TIGIT (T4 or CS19ME3-23) Abs' mIgG2a-DLE or mIgG2a-DE variants resulted in improved anti-tumor effects as compared to wild type mIgG2a, with especially pronounced improvements against the A20 tumors (FIG. 18E-F), which were found to be consistent with their enhanced ADCC effector functions as previously determined in Example 7 and FIG. 15. The mIgG2a-DANA variants lacking ADCC and ADCP functions in vitro exhibited minimal or no anti-tumor activity against both CT26 and A20 tumors (FIG. 18E-F). Recalling the finding that mIgG2a-DLE did not exert CDC function in vitro (as described in Example 7 above), it is conceivable that the observed anti-tumor effects of these variants do not require CDC function.

Pharmacokinetic Analysis

The present inventors examined the PK profile of the Fc variants of T4 Ab in BALB/c mice. 6-8 weeks old female BALB/c mice were used in this experiment. Blood was collected at different time points after a single intraperitoneal injection of testing Abs. Ab concentrations in serum were measured by an mTIGIT-binding ELISA.

It was found that the PK profile of the Fc variants of T4 Ab, T4-mIgG2a, T4-mIgG2a-DANA, as well as T4-hIgG1, all had comparable PK profiles, whereas T4-mIgG2a-DE and T4-mIgG2a-DLE had markedly faster clearance and shorter serum half-lives (FIG. 19), presumably because of lower stability of these Abs in vivo. Despite these apparently inferior PK profiles, recalling that T4-mIgG2a-DE and T4-mIgG2a-DLE showed stronger anti-tumor activity (FIG. 18E-F), it is concluded that the improved anti-tumor activities of these two Ab variants (T4-mIgG2a-DE and T4-mIgG2a-DLE) can be attributed to their superior effector functions.

Taken together, the above results demonstrated that FcγR-engagement mediated effector functions are important for anti-tumor activity of the anti-TIGIT Abs in vivo, as the Fc variants with enhanced effector functions exerted improved anti-tumor efficacy in vivo. Therefore, in one embodiment of the present application, the anti-TIGIT antibodies are Fc variants with enhanced effector functions.

Example 9. Involvement of CD8+ T and NK Cells in Anti-TIGIT Ab-Mediated Tumor Regression In this example, the present inventors sought to identify the immune cell types that contribute to the anti-tumor effect of the anti-TIGIT antibodies of the present application by conducting immune cell depletion studies in vivo.

Immune Cell Depletion in Vivo

For depletion of CD4 or CD8+ T cells, tumor-bearing BALB/c mice were injected with 200 μg of CD4-depleting Abs (clone GK1.5, BioXCell) or CD8-depleting Abs (clone 2.43, BioXCell) two days before T4 Ab treatment and twice per week.

For depletion of NK cells, mice were injected with 50 μg anti-Asialo-GM1 polyclonal Ab (Poly21460, Biolegend) one day before T4 Ab treatment and once every five days.

For depletion of neutrophils, mice were injected with 400 μg of anti-Ly6G monoclonal Ab (1A8 clone, BioXCell) two days before T4 Ab treatment and twice per week.

For depletion of macrophage, mice were injected with 100 μL Clodronate liposomes (FormuMax) one day before T4 Ab treatment and then once a week.

Depletion antibodies or reagents were given till the end of T4 Ab treatment for all of the immune cell depletion experiments. The efficiency of immune cell depletion methods described above was confirmed by using tumor-naïve BALB/c mice.

Involvement of CD4+ or CD8+ T Cell

First, the contribution of T cells was evaluated by using the aforementioned CT26 tumor model. It was observed that T4 Ab treatment induced effective CT26 tumor regression in WT BALB/c mice, but much less anti-tumor activity in T cell-deficient nude mice (FIG. 20A), clearly suggesting that T cells are required for the full therapeutic effect of T4 Ab.

Figure 20:
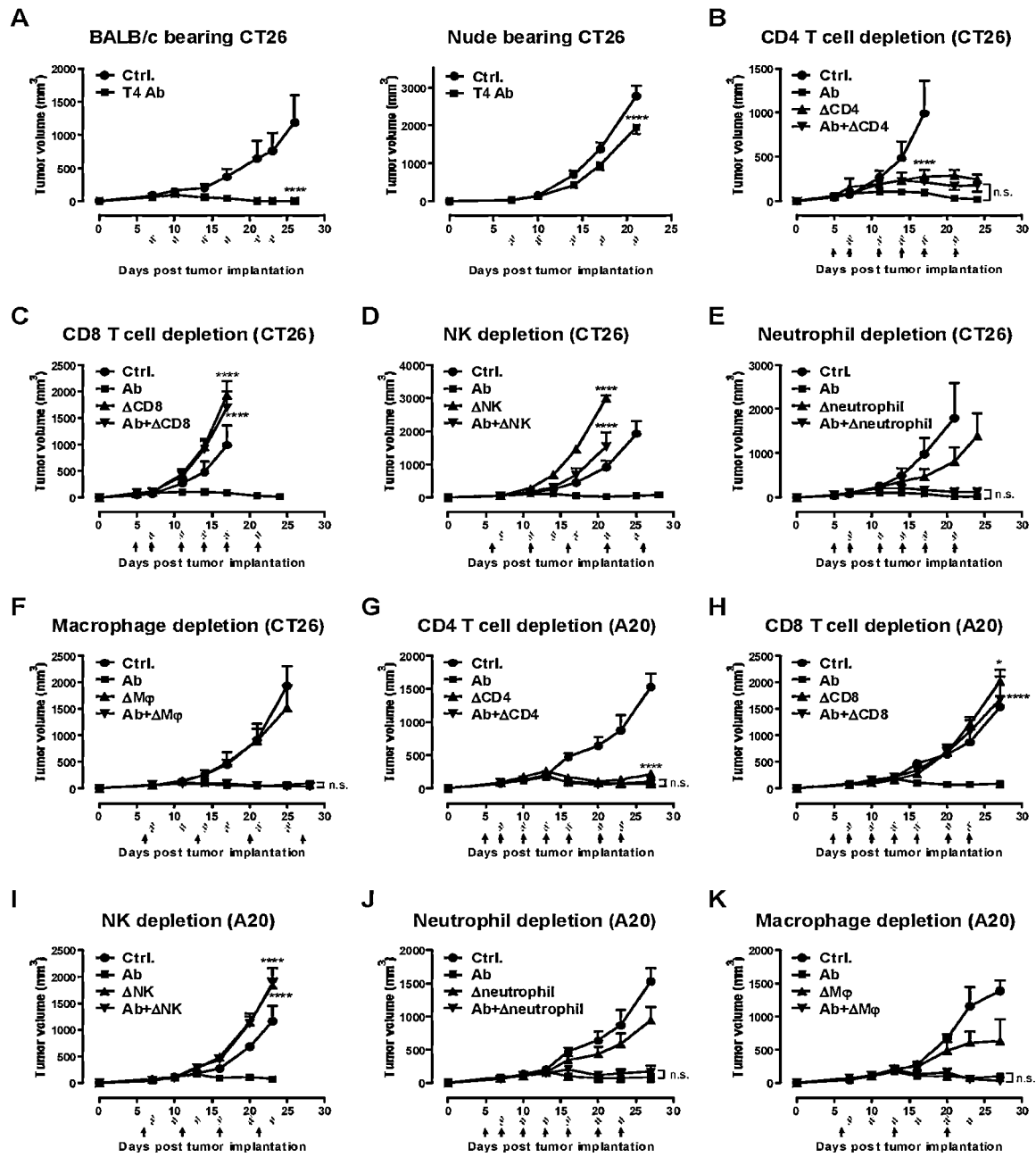

To identify which T cell subset(s) are involved in T4 Ab mediated tumor regression, CD4+ or CD8+ T cells were depleted by treating mice with an anti-CD4 or an anti-CD8 antibody, respectively, in BALB/c mice bearing established CT26 tumors two days prior to T4 Ab treatment. The depletion of CD4+ cells alone greatly repressed tumor growth regardless of T4 Ab treatment status, suggesting that anti-CD4 antibody treatment resulted in the removal of the immunosuppressive CD4+ cells and that CD4+ cells are apparently not required for the anti-tumor activity of the T4 Ab (FIG. 20B).

In contrast, tumors grew faster in mice from which CD8+ T cells were depleted as compared to non-depleted mice, regardless of T4 Ab treatment status, indicating that CD8+ T cells function as important effectors in natural anti-CT26 tumor immunity. Moreover, the depletion of CD8+ T cells completely abrogated the therapeutic effect of T4 Ab (FIG. 20C), supporting that CD8+ T cells are essential for the observed anti-tumor effects of the T4 Ab.

Involvement of NK Cells

Next, the potential roles of NK cells in the anti-tumor activity of T4 Ab by NK cell depletion was evaluated by using an anti-Asialo-GM1 antibody. NK cell depletion began one day before T4 Ab treatment in mice bearing established CT26 tumors, and continued till the end of T4 Ab treatment.

Similar to our observations with CD8+ cells, it was found that NKs here function as important natural anti-tumor effector cells. Specifically, tumors grew much faster in NK-depleted mice than in non-depleted mice. Moreover, the depletion of NK cells greatly impaired the therapeutic effect of T4 Ab treatment (FIG. 20D), indicating that the anti-tumor effects of the T4 Ab involve NK cells.

Involvement of Neutrophils and Macrophages

Also assessed were the roles of neutrophils and macrophages in the therapeutic effect of T4 Ab by depleting these cell types using an anti-Ly6G antibody (1A8 clone) to deplete neutrophils and using Clodronate Liposomes to deplete macrophages.

It was found that depletion of neutrophils or macrophages had no significant effect on the anti-tumor activity of T4 Ab, indicating they were unlikely involved in the anti-tumor effects of T4 Ab (FIG. 20E-F).

Depletion Studies in Syngeneic A20 Tumor Model Mice

Similar immune cell depletion studies were conducted in syngeneic BALB/c mice bearing A20 tumors. Similar results were observed as with the CT26 tumor model. Specifically, the depletion of CD8+ T or NK cells blocked or substantially reduced the anti-tumor effects of the T4 Ab, respectively, while depletion of CD4+ T, neutrophils, or macrophages had little or no effects on tumor outcomes following T4 Ab treatment (FIG. 20G-K).

Taken together, our results demonstrate that CD8+ T and NK immune cells contribute to the therapeutic effect of T4 Ab in both CT26 and A20 tumor-bearing mouse models.

Example 10. Cross-Protective and Durable Anti-Tumor Immune Memory Induced by the Treatment with the Anti-TIGIT Abs This example describes a durable anti-tumor immune memory, and the cross-protective effect after the treatment with the present anti-TIGIT antibodies as discovered by the present inventors.

Tumor Re-Challenge Studies

Mice with complete regressions of CT26 or A20 tumors after anti-TIGIT Abs' treatment were re-challenged with CT26, A20, or 4T1 tumors on day 80-100 after the initial tumor inoculation were subcutaneously (s.c.) inoculated with tumor cells ($1-3\times10^5$ CT26, A20, or 4T1) into the left flank. Age-matched naïve mice was used as controls and received same tumor implantations as the re-challenge groups. Tumor growth was monitored over time by measuring tumor volumes twice every week. Mouse sera were collected prior to tumor cell re-challenge and were confirmed to have no detectable anti-TIGIT Abs before the re-challenge.

Immune Memory Effect

In contrast to age-matched naïve mice, the anti-TIGIT Ab-cured mice were resistant to re-challenge with the same tumor. For example, mice cured of the CT26 were resistant to re-challenge with CT26, and the same was true for A20 tumor (FIGS. 21A and B).

Moreover, it was observed that mice with complete regressions of CT26 or A20 tumors had developed cross-tumor immunity rejecting both tumor types, but not to another different 4T1 tumor (FIGS. 21A and B).

These results demonstrate that treatment with the anti-TIGIT antibodies can result in protective and durable anti-tumor immune memory, and this memory is capable to cross-protect a different type of tumor that is responsive to the anti-TIGIT Abs' treatment, but not the one that is resistant to the anti-TIGIT Abs' treatment.

Example 11. Anti-TIGIT Ab Shows Potent Antitumor Effects Even at Low Dose

This example describes animal studies investigating the anti-tumor effect of the anti-TIGIT Abs at different doses.

All animal experiments were conducted following the National Guidelines for Housing and Care of Laboratory Animals in China and performed under the approved IACUC protocols at National Institute of Biological Sciences, Beijing.

For mouse tumor models, 6-8 weeks old female BALB/c mice were inoculated subcutaneously with $2\times10^5$ CT26 cells in the right flank. Based on similar mean CT26 tumor volumes (20-80 mm$^3$), mice were randomized into five groups (0.3 mg/kg group, 1 mg/kg group, 3 mg/kg group, 10 mg/kg group and no-treatment group as control; n=5-6/group) and received intraperitoneal injection of anti-TIGIT (CS19ME3-30-N-hIgG1-afuco) one time a week for 4 times. Tumor volume was measured with an electronic caliper and calculated using the modified ellipsoid formula ½×(length× width).

To investigate the anti-tumor activity of low and high doses of the anti-TIGIT Ab on tumor-bearing mouse models, the anti-tumor activities of Ab at different dosing amounts were compared in the immune-competent tumor-bearing mouse models. In BALB/c mice bearing CT26 tumor model, treatment with anti-TIGIT Ab (CS19ME3-30-N-hIgG1-afuco) showed potent anti-tumor activity even at the lowest dose of 0.3 mg/kg (FIG. 22). No obvious dose-dependency of the antibody was observed.

Example 12. Use of Anti-TIGIT Ab in Combination with Anti-PD-1 Ab or Anti-PD-L1 Ab This example investigates the combined use of the anti-TIGIT antibodies of the present application with an antibody against mPD-1 or mPD-L1 in two different tumor-bearing mouse models. Anti-mPD-1 Ab (RMP1-14) was from BioX-Cell, and anti-mPD-L1 Ab was selected from a phage display antibody library using the extracellular domain (ECD) of mouse PD-L1 (mPD-L1-ECD; Uniprot ID Q9EP73) as target. This Ab was expressed as anti-mPD-L 1-mIgG2a (mP4) and used in this assay.

All animal experiments were conducted following the National Guidelines for Housing and Care of Laboratory Animals in China and performed under the approved IACUC protocols at National Institute of Biological Sciences, Beijing.

For mouse tumor models, 6-8 weeks old female C57BL/6N or BALB/c mice were inoculated subcutaneously with $1\times10^5$ MC38 or $2\times10^5$ CT26 cells in the right flank.

MC38 tumor-bearing mice were randomized into groups (anti-TIGIT Ab treatment group (CS19ME3-30-N-mIgG2a, 10 mg/kg), anti-mPD-1 Ab treatment group (RMP1-14, 3 mg/kg), combined treatment group, and no-treatment group (PBS) as control; n=3-6/group) and received intraperitoneal injection of anti-TIGIT Ab and/or anti-mPD-1 (BioXCell, RMP1-14) or PBS.

Based on similar mean CT26 tumor volumes (120-270 mm³), mice were randomized into groups (n=3-6/group) and received intraperitoneal injection of anti-TIGIT Ab and/or anti-mPD-1 (BioXCell, RMP1-14), or anti-TIGIT Ab and/or homemade anti-mPD-L1 (mP4) two times per week for 4-6 times.

Tumor volume was measured with an electronic caliper and calculated using the modified ellipsoid formula ½× (length×width).

Figure 23:
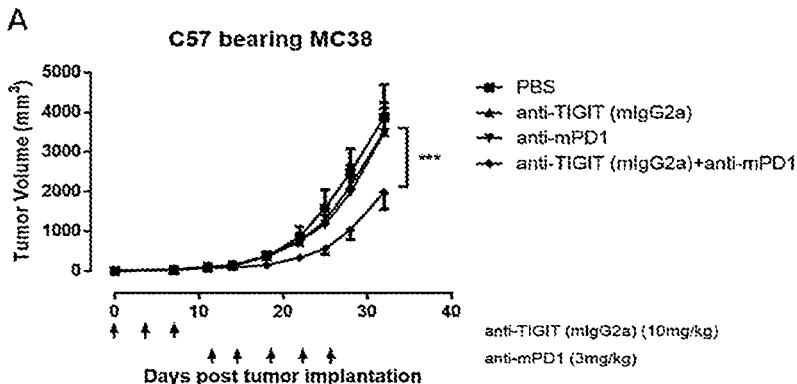
Figure 23:
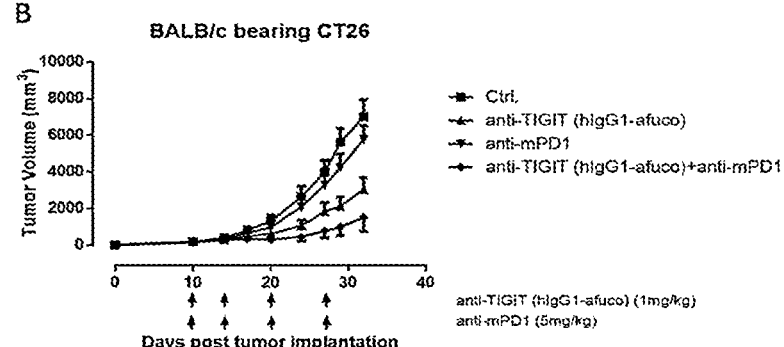
Figure 23:
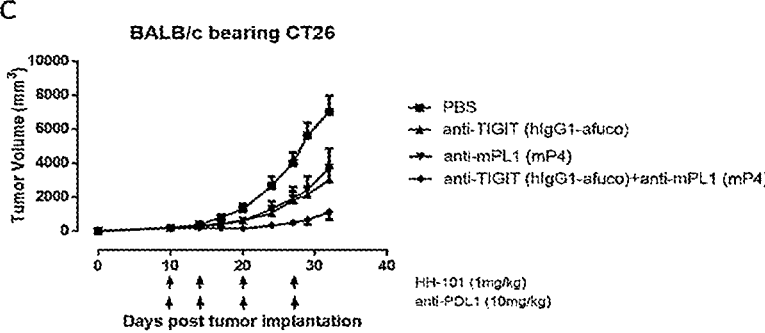

As shown in FIG. 23, the anti-TIGIT Abs (CS19ME3-30-N-mIgG2a and CS19ME3-30-N hIgG1-afuco) exhibited synergistic anti-tumor efficacy when combined with the anti-mPD-1 or PD-L1 antibodies in both MC38 and CT26 tumor-bearing mouse models. These observation suggests that the anti-TIGIT antibodies of the present disclosure may be used in a number of therapeutic applications, such as for the treatment of various cancers, either alone or in combination with another therapeutic agent, such as an anti-tumor agent, e.g. an anti-mPD-1 agent or anti-mPD-L1 agent.

REFERENCES

1. Harrison J L, Williams S C, Winter G, Nissim A. Screening of phage antibody libraries. Methods Enzymol 1996; 267:83-109.
2. McCafferty J, Griffiths A D, Winter G, Chiswell D J. Phage antibodies: filamentous phage displaying antibody variable domains. Nature 1990; 348:552-554.
3. Li D, He W, Liu X, Zheng S, Qi Y, Li H, Mao F, et al. A potent human neutralizing antibody Fc-dependently reduces established HBV infections. Elife 2017; 6.
4. Kiyotaka Nakano, Takeshi Yoshino, Jun-ichi Nezu, Hiroyuki Tsunoda, Tomoyuki Igawa, Hiroko Konishi, Megumi Tanaka, et al., inventors; Anti-glypican 3 antibody. U.S. Pat. No. 7,919,086 B2. 2005.
5. Stengel K F, Harden-Bowles K, Yu X, Rouge L, Yin J, Comps-Agrar L, Wiesmann C, et al. Structure of TIGIT immunoreceptor bound to poliovirus receptor reveals a cell-cell adhesion and signaling mechanism that requires cis-trans receptor clustering. Proc Natl Acad Sci U S A 2012; 109:5399-5404.
6. Liu S, Zhang H, Li M, Hu D, Li C, Ge B, Jin B, et al. Recruitment of Grb2 and SHIP1 by the ITT-like motif of TIGIT suppresses granule polarization and cytotoxicity of NK cells. Cell Death Differ 2013; 20:456-464.
7. Stanietsky N, Simic H, Arapovic J, Toporik A, Levy O, Novik A, Levine Z, et al. The interaction of TIGIT with PVR and PVRL2 inhibits human NK cell cytotoxicity. Proc Natl Acad Sci U S A 2009; 106:17858-17863.
8. Chen X, Allan D S, Krzewski K, Ge B, Kopcow H, Strominger J L. CD28-stimulated ERK2 phosphorylation is required for polarization of the microtubule organizing center and granules in YTS NK cells. Proc Natl Acad Sci U S A 2006; 103:10346-10351.
9. Shields R L, Namenuk A K, Hong K, Meng Y G, Rae J, Briggs J, Xie D, et al. High resolution mapping of the binding site on human IgG1 for Fc gamma RI, Fc gamma MI, Fc gamma RIII, and FcRn and design of IgG1 variants with improved binding to the Fc gamma R. J Biol Chem 2001; 276:6591-6604.
10. Wilson N S, Yang B, Yang A, Loeser S, Marsters S, Lawrence D, Li Y, et al. An Fc gamma receptor-dependent mechanism drives antibody-mediated target-receptor signaling in cancer cells. Cancer Cell 2011; 19:101-113.
11. Ferrari de Andrade L, Tay R E, Pan D, Luoma A M, Ito Y, Badrinath S, Tsoucas D, et al. Antibody-mediated inhibition of MICA and MICB shedding promotes NK cell-driven tumor immunity. Science 2018; 359:1537-1542.
12. Seshasayee D, Lee W P, Zhou M, Shu J, Suto E, Zhang J, Diehl L, et al. In vivo blockade of OX40 ligand inhibits thymic stromal lymphopoietin driven atopic inflammation. J Clin Invest 2007; 117:3868-3878.
13. Lo M, Kim H S, Tong R K, Bainbridge T W, Vernes J M, Zhang Y, Lin Y L, et al. Effector-attenuating Substitutions That Maintain Antibody Stability and Reduce Toxicity in Mice. J Biol Chem 2017; 292:3900-3908.
14. Lazar G A, Dang W, Karki S, Vafa O, Peng J S, Hyun L, Chan C, et al. Engineered antibody Fc variants with enhanced effector function. Proc Natl Acad Sci U S A 2006; 103:4005-4010.
15. Horton H M, Bernett M J, Peipp M, Pong E, Karki S, Chu S Y, Richards J O, et al. Fc-engineered anti-CD40 antibody enhances multiple effector functions and exhibits potent in vitro and in vivo antitumor activity against hematologic malignancies. Blood 2010; 116:3004-3012.
16. Horton H M, Bernett M J, Pong E, Peipp M, Karki S, Chu S Y, Richards J O, et al. Potent in vitro and in vivo activity of an Fc-engineered anti-CD19 monoclonal antibody against lymphoma and leukemia. Cancer Res 2008; 68:8049-8057.
17. Mohseni Nodehi S, Repp R, Kellner C, Brautigam J, Staudinger M, Schub N, Peipp M, et al. Enhanced ADCC activity of affinity maturated and Fc-engineered mini-antibodies directed against the AML stem cell antigen CD96. PLoS One 2012; 7:e42426.
18. Schewe D M, Alsadeq A, Sattler C, Lenk L, Vogiatzi F, Cario G, Vieth S, et al. An Fc-engineered CD19 antibody eradicates MRD in patient-derived MLL-rearranged acute lymphoblastic leukemia xenografts. Blood 2017; 130: 1543-1552.
19. Xu H, Guo H, Cheung I Y, Cheung N K. Antitumor Efficacy of Anti-GD2 IgG1 Is Enhanced by Fc Glyco-Engineering. Cancer Immunol Res 2016; 4:631-638.
20. Koerner S P, Andre M C, Leibold J S, Kousis P C, Kubler A, Pal M, Haen S P, et al. An Fc-optimized CD133 antibody for induction of NK cell reactivity against myeloid leukemia. Leukemia 2017; 31:459-469.
21. Kellner C, Otte A, Cappuzzello E, Klausz K, Peipp M. Modulating Cytotoxic Effector Functions by Fc Engineering to Improve Cancer Therapy. Transfus Med Hemother 2017; 44:327-336.
22. Shields R L, Lai J, Keck R, O'Connell L Y, Hong K, Meng Y G, Weikert S H, et al. Lack of fucose on human IgG1 N-linked oligosaccharide improves binding to human Fcgamma RIII and antibody-dependent cellular toxicity. J Biol Chem 2002; 277:26733-26740.
23. Nimmerjahn F, Ravetch J V. Fcgamma receptors: old friends and new family members. Immunity 2006; 24:19-28.
24. Nimmerjahn F, Ravetch J V. Divergent immunoglobulin g subclass activity through selective Fc receptor binding. Science 2005; 310:1510-1512.
25. Hsieh Y T, Aggarwal P, Cirelli D, Gu L, Surowy T, Mozier N M. Characterization of FcgammaRIIIA effector cells used in in vitro ADCC bioassay: Comparison of primary NK cells with engineered NK-92 and Jurkat T cells. J Immunol Methods 2017; 441:56-66.

The invention claimed is:

1. An isolated antibody or an antigen-binding fragment thereof which binds to human TIGIT (T cell immunoreceptor with Ig and ITIM domain) and mouse TIGIT, comprising any of the following:

(1) a VH comprising an HCDR1 having the amino acid sequence of SEQ ID NO: 18, an HCDR2 having the amino acid sequence of SEQ ID NO: 19, and an HCDR3 having the amino acid sequence of SEQ ID NO: 20; and a VL comprising an LCDR1 having the amino acid sequence of SEQ ID NO: 23, an LCDR2 having the amino acid sequence of SEQ ID NO: 24, and an LCDR3 having the amino acid sequence of SEQ ID NO: 25;

(2) a VH comprising an HCDRI having the amino acid sequence of SEQ ID NO: 18, an HCDR2 having the amino acid sequence of SEQ ID NO: 19, and an HCDR3 having the amino acid sequence of SEQ ID NO: 20; and a VL comprising an LCDR1 having the amino acid sequence of SEQ ID NO: 30, an LCDR2 having the amino acid sequence of SEQ ID NO: 31, and an LCDR3 having the amino acid sequence of SEQ ID NO: 32; or (3) a VH comprising an HCDR1 having the amino acid sequence of SEQ ID NO: 18, an HCDR2 having the amino acid sequence of SEQ ID NO: 19, and an HCDR3 having the amino acid sequence of SEQ ID NO: 20; and a VL comprising an LCDR1 having the amino acid sequence of SEQ ID NO: 15, an LCDR2 having the amino acid sequence of SEQ ID NO: 16, and an LCDR3 having the amino acid sequence of SEQ ID NO: 17.

2. The antibody or antigen-binding fragment thereof according to claim 1, wherein (1) the VH comprising an amino acid sequence having at least 95%, 96%, 97%, 98%, 99% or 100% identity to SEQ ID NO: 27; and/or the VL comprising an amino acid sequence having at least 95%, 96%, 97%, 98%, 99% or 100% identity to SEQ ID NO: 26; or (2) the VH comprising an amino acid sequence having at least 95%, 96%, 97%, 98%, 99% or 100% identity to SEQ ID NO: 34; and/or the VL comprising an amino acid sequence having at least 95%, 96%, 97%, 98%, 99% or 100% identity to SEQ ID NO: 33.

3. The antibody or antigen-binding fragment thereof according to claim 1, wherein (1) the VH comprising an amino acid of SEQ ID NO: 27; and/or a light chain variable domain (VL) comprising an amino acid sequence of SEQ ID NO: 26; or (2) the VH comprising an amino acid sequence of SEQ ID NO: 34; and/or the VL comprising an amino acid sequence of SEQ ID NO: 33.

4. The antibody or antigen-binding fragment thereof according to claim 1, wherein the antibody or antigen-binding fragment thereof is a human IgG1 antibody or variant thereof having enhanced effector function or without effector functions.

5. The antibody or antigen-binding fragment thereof according to claim 1, further modified by changing the Fc region so as to (1) enhance ADCC function, (2) enhance ADCP function; and/or (3) reduce or eliminate CDC function, as compared to the antibody without such modification.

6. The antibody or antigen-binding fragment thereof according to claim 1, wherein the antibody is an afucosylated antibody or antigen-binding fragment thereof.

7. The antibody or antigen-binding fragment thereof according to claim 6, wherein the afucosylated antibody or antigen-binding fragment thereof has increased effector functions as compared to its fucosylated counterpart.

8. An isolated nucleic acid encoding the antibody or antigen-binding fragment thereof according to claim 1.

9. The nucleic acid according to claim 8, comprising (1) a nucleotide sequence having at least 95%, 96%, 97%, 98%, 99% or 100% identity to the nucleotide sequence of SEQ ID NO: 29, and/or a nucleotide sequence having at least 95%, 96%, 97%, 98%, 99% or 100% identity to the nucleotide sequence of SEQ ID NO: 28; or (2) a nucleotide sequence having at least 95%, 96%, 97%, 98%, 99% or 100% identity to the nucleotide sequence of SEQ ID NO: 36, and/or a nucleotide sequence having at least 95%, 96%, 97%, 98%, 99% or 100% identity to the nucleotide sequence of SEQ ID NO: 35.

10. A vector comprising the nucleic acid according to claim 8.

11. A cell comprising the nucleic acid according to claim 8.

12. A method of treating cancer or viral infection in a subject in need thereof, comprising administering to the subject a therapeutically effective amount of the antibody or the antigen-binding fragment thereof according to claim 1.

13. A method of treating cancer or viral infection in a subject in need thereof, comprising administering to the subject a therapeutically effective amount of the antibody or antigen-binding fragment thereof according to claim 1 in combination with an additional therapeutic agent to the subject.

14. The method according to claim 13, wherein the additional therapeutic agent is selected from a group consisting of an anti-PD-1 antibody, an anti-PD-L1 antibody, an anti-LAG-3 antibody, an anti-CTLA-4 antibody, and an anti-TIM3 antibody.

15. The method according to claim 12, wherein the antibody or antigen-binding fragment thereof blocks the binding of TIGIT to CD155 and exerts effector function.

16. The antibody or antigen-binding fragment thereof according to claim 3, wherein the antibody is an afucosylated antibody or antigen-binding fragment thereof.

17. The antibody or antigen-binding fragment thereof according to claim 16, wherein the afucosylated antibody or antigen-binding fragment thereof has increased effector functions as compared to its fucosylated counterpart.

18. A vector comprising the nucleic acid according to claim 9.

19. A cell comprising the vector according to claim 10.

20. The cell according to claim 11, wherein the cell is an FUT8 knockout cell.

21. The cell according to claim 20, wherein the cell is an FUT8 knockout CHO cell.

\* \* \* \* \*

SEQUENCE LISTING

<160> NUMBER OF SEQ ID NOS: 36

<210> SEQ ID NO 1
<211> LENGTH: 11
<212> TYPE: PRT
<213> ORGANISM: Artificial Sequence
<220> FEATURE:
<223> OTHER INFORMATION: T4 consensus sequence LCDR1
<220> FEATURE:
<221> NAME/KEY: MISC_FEATURE
<222> LOCATION: (5)..(5)
<223> OTHER INFORMATION: X is S, I or N
<220> FEATURE:
<221> NAME/KEY: MISC_FEATURE
<222> LOCATION: (7)..(7)
<223> OTHER INFORMATION: X is S, K, N, or T
<220> FEATURE:
<221> NAME/KEY: MISC_FEATURE
<222> LOCATION: (8)..(8)
<223> OTHER INFORMATION: X is S, K, N, or R

<400> SEQUENCE: 1

Arg Ala Ser Gln Xaa Ile Xaa Xaa Tyr Leu Asn
1               5                   10

<210> SEQ ID NO 2
<211> LENGTH: 7
<212> TYPE: PRT
<213> ORGANISM: Artificial Sequence
<220> FEATURE:
<223> OTHER INFORMATION: T4 consensus sequence LCDR2
<220> FEATURE:
<221> NAME/KEY: MISC_FEATURE
<222> LOCATION: (1)..(1)
<223> OTHER INFORMATION: X is A, L, S, or T
<220> FEATURE:
<221> NAME/KEY: MISC_FEATURE
<222> LOCATION: (2)..(2)
<223> OTHER INFORMATION: X is A, or T
<220> FEATURE:
<221> NAME/KEY: MISC_FEATURE
<222> LOCATION: (3)..(3)
<223> OTHER INFORMATION: X is S, or Y
<220> FEATURE:
<221> NAME/KEY: MISC_FEATURE
<222> LOCATION: (4)..(4)
<223> OTHER INFORMATION: X is S, I, or T
<220> FEATURE:
<221> NAME/KEY: MISC_FEATURE
<222> LOCATION: (6)..(6)
<223> OTHER INFORMATION: X is Q, P, or E
<220> FEATURE:
<221> NAME/KEY: MISC_FEATURE
<222> LOCATION: (7)..(7)
<223> OTHER INFORMATION: X is S, N, or R

<400> SEQUENCE: 2

Xaa Xaa Xaa Xaa Leu Xaa Xaa
1               5

<210> SEQ ID NO 3
<211> LENGTH: 9
<212> TYPE: PRT
<213> ORGANISM: Artificial Sequence
<220> FEATURE:
<223> OTHER INFORMATION: T4 consensus sequence LCDR3
<220> FEATURE:
<221> NAME/KEY: MISC_FEATURE
<222> LOCATION: (2)..(2)
<223> OTHER INFORMATION: X is Q, or H
<220> FEATURE:
<221> NAME/KEY: MISC_FEATURE
<222> LOCATION: (4)..(4)
<223> OTHER INFORMATION: X is Y, or H

```
<220> FEATURE:
<221> NAME/KEY: MISC_FEATURE
<222> LOCATION: (5)..(5)
<223> OTHER INFORMATION: X is S, A, T, or N
<220> FEATURE:
<221> NAME/KEY: MISC_FEATURE
<222> LOCATION: (6)..(6)
<223> OTHER INFORMATION: X is T, P, or V
<220> FEATURE:
<221> NAME/KEY: MISC_FEATURE
<222> LOCATION: (7)..(7)
<223> OTHER INFORMATION: X is P, or S
<220> FEATURE:
<221> NAME/KEY: MISC_FEATURE
<222> LOCATION: (9)..(9)
<223> OTHER INFORMATION: X is T, S, or I

<400> SEQUENCE: 3

Gln Xaa Ser Xaa Xaa Xaa Xaa Ile Xaa
1               5

<210> SEQ ID NO 4
<211> LENGTH: 5
<212> TYPE: PRT
<213> ORGANISM: Artificial Sequence
<220> FEATURE:
<223> OTHER INFORMATION: T4 HCDR1

<400> SEQUENCE: 4

Asp Tyr Tyr Trp Thr
1               5

<210> SEQ ID NO 5
<211> LENGTH: 16
<212> TYPE: PRT
<213> ORGANISM: Artificial Sequence
<220> FEATURE:
<223> OTHER INFORMATION: T4 HCDR2

<400> SEQUENCE: 5

Glu Ile Thr His Ser Gly Ser Ala Asp Tyr Asn Pro Ser Leu Lys Ser
1               5                   10                  15

<210> SEQ ID NO 6
<211> LENGTH: 24
<212> TYPE: PRT
<213> ORGANISM: Artificial Sequence
<220> FEATURE:
<223> OTHER INFORMATION: T4 HCDR3

<400> SEQUENCE: 6

Gly Leu Lys Leu Phe Arg Trp Lys Lys Thr Thr Val Thr Thr Phe Pro
1               5                   10                  15

Pro Tyr Tyr Tyr Gly Met Asp Val
            20

<210> SEQ ID NO 7
<211> LENGTH: 107
<212> TYPE: PRT
<213> ORGANISM: Artificial Sequence
<220> FEATURE:
<223> OTHER INFORMATION: T4 VL consensus sequence
<220> FEATURE:
<221> NAME/KEY: MISC_FEATURE
<222> LOCATION: (3)..(3)
<223> OTHER INFORMATION: X is Q, or V
<220> FEATURE:
<221> NAME/KEY: MISC_FEATURE
<222> LOCATION: (4)..(4)
<223> OTHER INFORMATION: X is M, or L
```

-continued

```
<220> FEATURE:
<221> NAME/KEY: MISC_FEATURE
<222> LOCATION: (15)..(15)
<223> OTHER INFORMATION: X is V, I, or L
<220> FEATURE:
<221> NAME/KEY: MISC_FEATURE
<222> LOCATION: (18)..(18)
<223> OTHER INFORMATION: X is R, or T
<220> FEATURE:
<221> NAME/KEY: MISC_FEATURE
<222> LOCATION: (19)..(19)
<223> OTHER INFORMATION: X is V, or I
<220> FEATURE:
<221> NAME/KEY: MISC_FEATURE
<222> LOCATION: (20)..(20)
<223> OTHER INFORMATION: X is T, or A
<220> FEATURE:
<221> NAME/KEY: MISC_FEATURE
<222> LOCATION: (22)..(22)
<223> OTHER INFORMATION: X is T, or S
<220> FEATURE:
<221> NAME/KEY: MISC_FEATURE
<222> LOCATION: (28)..(28)
<223> OTHER INFORMATION: X is S, I, or N
<220> FEATURE:
<221> NAME/KEY: MISC_FEATURE
<222> LOCATION: (30)..(30)
<223> OTHER INFORMATION: X is S, K, N, or T
<220> FEATURE:
<221> NAME/KEY: MISC_FEATURE
<222> LOCATION: (31)..(31)
<223> OTHER INFORMATION: X is S, K, N, or R
<220> FEATURE:
<221> NAME/KEY: MISC_FEATURE
<222> LOCATION: (39)..(39)
<223> OTHER INFORMATION: X is K, or R
<220> FEATURE:
<221> NAME/KEY: MISC_FEATURE
<222> LOCATION: (43)..(43)
<223> OTHER INFORMATION: X is R, or S
<220> FEATURE:
<221> NAME/KEY: MISC_FEATURE
<222> LOCATION: (45)..(45)
<223> OTHER INFORMATION: X is K, E, or T
<220> FEATURE:
<221> NAME/KEY: MISC_FEATURE
<222> LOCATION: (48)..(48)
<223> OTHER INFORMATION: X is I, or V
<220> FEATURE:
<221> NAME/KEY: MISC_FEATURE
<222> LOCATION: (49)..(49)
<223> OTHER INFORMATION: X is Y, or S
<220> FEATURE:
<221> NAME/KEY: MISC_FEATURE
<222> LOCATION: (50)..(50)
<223> OTHER INFORMATION: X is A, L, S, or T
<220> FEATURE:
<221> NAME/KEY: MISC_FEATURE
<222> LOCATION: (51)..(51)
<223> OTHER INFORMATION: X is A, or T
<220> FEATURE:
<221> NAME/KEY: MISC_FEATURE
<222> LOCATION: (52)..(52)
<223> OTHER INFORMATION: X is S, or Y
<220> FEATURE:
<221> NAME/KEY: MISC_FEATURE
<222> LOCATION: (53)..(53)
<223> OTHER INFORMATION: X is S, I, or T
<220> FEATURE:
<221> NAME/KEY: MISC_FEATURE
<222> LOCATION: (55)..(55)
<223> OTHER INFORMATION: X is Q, P, or E
<220> FEATURE:
<221> NAME/KEY: MISC_FEATURE
<222> LOCATION: (56)..(56)
<223> OTHER INFORMATION: X is S, N, or R
<220> FEATURE:
<221> NAME/KEY: MISC_FEATURE
<222> LOCATION: (63)..(63)
```

-continued

```
<223> OTHER INFORMATION: X is S, or R
<220> FEATURE:
<221> NAME/KEY: MISC_FEATURE
<222> LOCATION: (66)..(66)
<223> OTHER INFORMATION: X is G, or R
<220> FEATURE:
<221> NAME/KEY: MISC_FEATURE
<222> LOCATION: (68)..(68)
<223> OTHER INFORMATION: X is G, or E
<220> FEATURE:
<221> NAME/KEY: MISC_FEATURE
<222> LOCATION: (76)..(76)
<223> OTHER INFORMATION: X is S, or N
<220> FEATURE:
<221> NAME/KEY: MISC_FEATURE
<222> LOCATION: (79)..(79)
<223> OTHER INFORMATION: X is Q, or E
<220> FEATURE:
<221> NAME/KEY: MISC_FEATURE
<222> LOCATION: (84)..(84)
<223> OTHER INFORMATION: X is A, or G
<220> FEATURE:
<221> NAME/KEY: MISC_FEATURE
<222> LOCATION: (87)..(87)
<223> OTHER INFORMATION: X is Y, or F
<220> FEATURE:
<221> NAME/KEY: MISC_FEATURE
<222> LOCATION: (90)..(90)
<223> OTHER INFORMATION: X is Q, or H
<220> FEATURE:
<221> NAME/KEY: MISC_FEATURE
<222> LOCATION: (92)..(92)
<223> OTHER INFORMATION: X is Y, or H
<220> FEATURE:
<221> NAME/KEY: MISC_FEATURE
<222> LOCATION: (93)..(93)
<223> OTHER INFORMATION: X is S, A, T, or N
<220> FEATURE:
<221> NAME/KEY: MISC_FEATURE
<222> LOCATION: (94)..(94)
<223> OTHER INFORMATION: X is T, P, or V
<220> FEATURE:
<221> NAME/KEY: MISC_FEATURE
<222> LOCATION: (95)..(95)
<223> OTHER INFORMATION: X is P, or S
<220> FEATURE:
<221> NAME/KEY: MISC_FEATURE
<222> LOCATION: (97)..(97)
<223> OTHER INFORMATION: X is T, S, or I
<220> FEATURE:
<221> NAME/KEY: MISC_FEATURE
<222> LOCATION: (100)..(100)
<223> OTHER INFORMATION: X is Q, G, or P
<220> FEATURE:
<221> NAME/KEY: MISC_FEATURE
<222> LOCATION: (101)..(101)
<223> OTHER INFORMATION: X is G, or R
<220> FEATURE:
<221> NAME/KEY: MISC_FEATURE
<222> LOCATION: (103)..(103)
<223> OTHER INFORMATION: X is R, or K
<220> FEATURE:
<221> NAME/KEY: MISC_FEATURE
<222> LOCATION: (105)..(105)
<223> OTHER INFORMATION: X is E, or D

<400> SEQUENCE: 7

Asp Ile Xaa Xaa Thr Gln Ser Pro Ser Ser Leu Ser Ala Ser Xaa Gly
1               5                   10                  15

Asp Xaa Xaa Xaa Ile Xaa Cys Arg Ala Ser Gln Xaa Ile Xaa Xaa Tyr
            20                  25                  30

Leu Asn Trp Tyr Gln Gln Xaa Pro Gly Lys Xaa Pro Xaa Leu Leu Xaa
        35                  40                  45

Xaa Xaa Xaa Xaa Xaa Leu Xaa Xaa Gly Val Pro Ser Arg Phe Xaa Gly
    50                  55                  60
```

-continued

```
Ser Xaa Ser Xaa Thr Asp Phe Thr Leu Thr Ile Xaa Ser Leu Xaa Pro
65                  70                  75                  80

Glu Asp Phe Xaa Thr Tyr Xaa Cys Gln Xaa Ser Xaa Xaa Xaa Xaa Ile
                    85                  90                  95

Xaa Phe Gly Xaa Xaa Thr Xaa Leu Xaa Ile Lys
            100                 105
```

```
<210> SEQ ID NO 8
<211> LENGTH: 132
<212> TYPE: PRT
<213> ORGANISM: Artificial Sequence
<220> FEATURE:
<223> OTHER INFORMATION: T4 VH

<400> SEQUENCE: 8

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Asn Asp Tyr
            20                  25                  30

Tyr Trp Thr Trp Ile Arg Gln Ala Pro Gly Lys Gly Leu Glu Trp Ile
        35                  40                  45

Gly Glu Ile Thr His Ser Gly Ser Ala Asp Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Arg Ser Val Thr Ala Ala Asp Thr Ala Val Tyr Tyr Cys Ala
            85                  90                  95

Arg Gly Leu Lys Leu Phe Arg Trp Lys Lys Thr Thr Val Thr Thr Phe
            100                 105                 110

Pro Pro Tyr Tyr Tyr Gly Met Asp Val Trp Gly Gln Gly Thr Thr Val
            115                 120                 125

Thr Val Ser Ser
        130
```

```
<210> SEQ ID NO 9
<211> LENGTH: 11
<212> TYPE: PRT
<213> ORGANISM: Artificial Sequence
<220> FEATURE:
<223> OTHER INFORMATION: T4M LCDR1

<400> SEQUENCE: 9

Arg Ala Ser Gln Ser Ile Ser Ser Tyr Leu Asn
1               5                   10
```

```
<210> SEQ ID NO 10
<211> LENGTH: 7
<212> TYPE: PRT
<213> ORGANISM: Artificial Sequence
<220> FEATURE:
<223> OTHER INFORMATION: T4M LCDR2

<400> SEQUENCE: 10

Ser Ala Tyr Ser Leu Gln Ser
1               5
```

```
<210> SEQ ID NO 11
<211> LENGTH: 9
<212> TYPE: PRT
<213> ORGANISM: Artificial Sequence
<220> FEATURE:
```

<223> OTHER INFORMATION: T4M LCDR3

<400> SEQUENCE: 11

Gln Gln Ser Tyr Ser Thr Pro Ile Thr
1               5

<210> SEQ ID NO 12
<211> LENGTH: 107
<212> TYPE: PRT
<213> ORGANISM: Artificial Sequence
<220> FEATURE:
<223> OTHER INFORMATION: T4M VL

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ser Ala Tyr Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Arg Leu Glu Ile Lys
            100                 105

<210> SEQ ID NO 13
<211> LENGTH: 321
<212> TYPE: DNA
<213> ORGANISM: Artificial Sequence
<220> FEATURE:
<223> OTHER INFORMATION: T4M VL nucleotide
<220> FEATURE:
<221> NAME/KEY: misc_feature
<222> LOCATION: (70)..(102)
<220> FEATURE:
<221> NAME/KEY: misc_feature
<222> LOCATION: (148)..(168)
<220> FEATURE:
<221> NAME/KEY: misc_feature
<222> LOCATION: (265)..(291)

<400> SEQUENCE: 13
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctattct gcatacagtt tgcaaagtgg ggtcccatca     180
aggttcagtg gcagtggatc tgggacagat ttcactctca ccatcagcag tctgcaacct     240
gaagattttg caacttacta ctgtcaacag agttacagta ccccgatcac cttcggccaa     300
gggacacgac tggagattaa a                                               321

<210> SEQ ID NO 14
<211> LENGTH: 396
<212> TYPE: DNA
<213> ORGANISM: Artificial Sequence
<220> FEATURE:
<223> OTHER INFORMATION: T4 VH nucleotide
<220> FEATURE:
<221> NAME/KEY: misc_feature
<222> LOCATION: (91)..(105)

-continued

```
<223> OTHER INFORMATION: HCDR1 coding sequence
<220> FEATURE:
<221> NAME/KEY: misc_feature
<222> LOCATION: (148)..(195)
<223> OTHER INFORMATION: HCDR2 coding sequence
<220> FEATURE:
<221> NAME/KEY: misc_feature
<222> LOCATION: (292)..(363)
<223> OTHER INFORMATION: HCDR3 coding sequence

<400> SEQUENCE: 14
caggtgcagc tacagcagtg gggcgcagga ctgttgaagc cttcggagac cctgtccctc        60
acctgcgctg tctatggtgg gtcattcaat gattactact ggacctggat ccgccaggcc       120
ccagggaagg ggctggagtg gattggggaa atcactcaca gtggaagcgc cgactacaat       180
ccgtccctca agagtcgagt caccatatca gtagacacgt ccaagaacca gttctccctg       240
aagctgaggt ctgtgaccgc cgcggacacg gctgtgtatt actgtgcgag agggctcaaa       300 cttttttcgtt ggaaaaagac tacggtgact acgttccccc cttactacta cggtatggac       360
gtctggggcc aagggaccac ggtcaccgtc tcctca                                  396

<210> SEQ ID NO 15
<211> LENGTH: 14
<212> TYPE: PRT
<213> ORGANISM: Artificial Sequence
<220> FEATURE:
<223> OTHER INFORMATION: hm7 LCDR1 consensus sequence
<220> FEATURE:
<221> NAME/KEY: MISC_FEATURE
<222> LOCATION: (3)..(3)
<223> OTHER INFORMATION: X is T, or S
<220> FEATURE:
<221> NAME/KEY: MISC_FEATURE
<222> LOCATION: (4)..(4)
<223> OTHER INFORMATION: X is S, I, G, or N
<220> FEATURE:
<221> NAME/KEY: MISC_FEATURE
<222> LOCATION: (5)..(5)
<223> OTHER INFORMATION: X is S, or R
<220> FEATURE:
<221> NAME/KEY: MISC_FEATURE
<222> LOCATION: (9)..(9)
<223> OTHER INFORMATION: X is G, R, S, or absent
<220> FEATURE:
<221> NAME/KEY: MISC_FEATURE
<222> LOCATION: (10)..(10)
<223> OTHER INFORMATION: X is Y, or H
<220> FEATURE:
<221> NAME/KEY: MISC_FEATURE
<222> LOCATION: (11)..(11)
<223> OTHER INFORMATION: X is N, P, D, or S
<220> FEATURE:
<221> NAME/KEY: MISC_FEATURE
<222> LOCATION: (12)..(12)
<223> OTHER INFORMATION: X is F, or Y

<400> SEQUENCE: 15

Thr Gly Xaa Xaa Xaa Asp Val Gly Xaa Xaa Xaa Xaa Val Ser
1               5                   10

<210> SEQ ID NO 16
<211> LENGTH: 7
<212> TYPE: PRT
<213> ORGANISM: Artificial Sequence
<220> FEATURE:
<223> OTHER INFORMATION: hm7 cons LCDR2
<220> FEATURE:
<221> NAME/KEY: MISC_FEATURE
<222> LOCATION: (1)..(1)
<223> OTHER INFORMATION: X is E, D, Y, A, or G
<220> FEATURE:
```

```
<221> NAME/KEY: MISC_FEATURE
<222> LOCATION: (2)..(2)
<223> OTHER INFORMATION: X is V, A, or G
<220> FEATURE:
<221> NAME/KEY: MISC_FEATURE
<222> LOCATION: (3)..(3)
<223> OTHER INFORMATION: X is S, T, N, H, G, I, or R
<220> FEATURE:
<221> NAME/KEY: MISC_FEATURE
<222> LOCATION: (4)..(4)
<223> OTHER INFORMATION: X is K, or N
<220> FEATURE:
<221> NAME/KEY: MISC_FEATURE
<222> LOCATION: (6)..(6)
<223> OTHER INFORMATION: X is P, or A

<400> SEQUENCE: 16

Xaa Xaa Xaa Xaa Arg Xaa Ser
1               5

<210> SEQ ID NO 17
<211> LENGTH: 12
<212> TYPE: PRT
<213> ORGANISM: Artificial Sequence
<220> FEATURE:
<223> OTHER INFORMATION: hm7 cons LCDR3
<220> FEATURE:
<221> NAME/KEY: MISC_FEATURE
<222> LOCATION: (4)..(4)
<223> OTHER INFORMATION: X is S, R, A, T, or G
<220> FEATURE:
<221> NAME/KEY: MISC_FEATURE
<222> LOCATION: (5)..(5)
<223> OTHER INFORMATION: X is S, G, R, or absent
<220> FEATURE:
<221> NAME/KEY: MISC_FEATURE
<222> LOCATION: (6)..(6)
<223> OTHER INFORMATION: X is S, M, P, or absent
<220> FEATURE:
<221> NAME/KEY: MISC_FEATURE
<222> LOCATION: (7)..(7)
<223> OTHER INFORMATION: X is G, S, P, T, N, or E
<220> FEATURE:
<221> NAME/KEY: MISC_FEATURE
<222> LOCATION: (8)..(8)
<223> OTHER INFORMATION: X is S, H, G, T, N, or P
<220> FEATURE:
<221> NAME/KEY: MISC_FEATURE
<222> LOCATION: (9)..(9)
<223> OTHER INFORMATION: X is T, Q, A, P, G, V, K, or absent
<220> FEATURE:
<221> NAME/KEY: MISC_FEATURE
<222> LOCATION: (10)..(10)
<223> OTHER INFORMATION: X is R, S, T, G, L, K, N, H, A, or absent
<220> FEATURE:
<221> NAME/KEY: MISC_FEATURE
<222> LOCATION: (11)..(11)
<223> OTHER INFORMATION: X is L, or V
<220> FEATURE:
<221> NAME/KEY: MISC_FEATURE
<222> LOCATION: (12)..(12)
<223> OTHER INFORMATION: X is V, L, or I

<400> SEQUENCE: 17

Ser Ser Tyr Xaa Xaa Xaa Xaa Xaa Xaa Xaa Xaa Xaa
1               5                   10

<210> SEQ ID NO 18
<211> LENGTH: 5
<212> TYPE: PRT
<213> ORGANISM: Artificial Sequence
<220> FEATURE:
<223> OTHER INFORMATION: hm7 cons HCDR1

<400> SEQUENCE: 18
```

-continued

```
Ser Tyr Ala Met His
1               5

<210> SEQ ID NO 19
<211> LENGTH: 17
<212> TYPE: PRT
<213> ORGANISM: Artificial Sequence
<220> FEATURE:
<223> OTHER INFORMATION: hm7 cons HCDR2

<400> SEQUENCE: 19

Val Ile Ser Tyr Asp Gly Ser Asn Lys Tyr Tyr Ala Asp Ser Val Lys
1               5                   10                  15

Gly

<210> SEQ ID NO 20
<211> LENGTH: 15
<212> TYPE: PRT
<213> ORGANISM: Artificial Sequence
<220> FEATURE:
<223> OTHER INFORMATION: hm7 cons HCDR3

<400> SEQUENCE: 20

Leu Glu Gly Gly Gly Arg Tyr Tyr Asp Phe Trp Ser Ala Asp Tyr
1               5                   10                  15

<210> SEQ ID NO 21
<211> LENGTH: 112
<212> TYPE: PRT
<213> ORGANISM: Artificial Sequence
<220> FEATURE:
<223> OTHER INFORMATION: hm7 cons VL
<220> FEATURE:
<221> NAME/KEY: MISC_FEATURE
<222> LOCATION: (2)..(2)
<223> OTHER INFORMATION: X is S, A or P
<220> FEATURE:
<221> NAME/KEY: MISC_FEATURE
<222> LOCATION: (3)..(3)
<223> OTHER INFORMATION: X is A, G, or V
<220> FEATURE:
<221> NAME/KEY: MISC_FEATURE
<222> LOCATION: (8)..(8)
<223> OTHER INFORMATION: X is R, A, or P
<220> FEATURE:
<221> NAME/KEY: MISC_FEATURE
<222> LOCATION: (10)..(10)
<223> OTHER INFORMATION: X is V, or A
<220> FEATURE:
<221> NAME/KEY: MISC_FEATURE
<222> LOCATION: (12)..(12)
<223> OTHER INFORMATION: X is G, A, or E
<220> FEATURE:
<221> NAME/KEY: MISC_FEATURE
<222> LOCATION: (18)..(18)
<223> OTHER INFORMATION: X is V, or I
<220> FEATURE:
<221> NAME/KEY: MISC_FEATURE
<222> LOCATION: (20)..(20)
<223> OTHER INFORMATION: X is I, or V
<220> FEATURE:
<221> NAME/KEY: MISC_FEATURE
<222> LOCATION: (25)..(25)
<223> OTHER INFORMATION: X is T, or S
<220> FEATURE:
<221> NAME/KEY: MISC_FEATURE
<222> LOCATION: (26)..(26)
<223> OTHER INFORMATION: X is S, I, G, or N
<220> FEATURE:
<221> NAME/KEY: MISC_FEATURE
<222> LOCATION: (27)..(27)
<223> OTHER INFORMATION: X is S, or R
```

-continued

```
<220> FEATURE:
<221> NAME/KEY: MISC_FEATURE
<222> LOCATION: (31)..(31)
<223> OTHER INFORMATION: X is G, R, S, or absent
<220> FEATURE:
<221> NAME/KEY: MISC_FEATURE
<222> LOCATION: (32)..(32)
<223> OTHER INFORMATION: X is Y, or H
<220> FEATURE:
<221> NAME/KEY: MISC_FEATURE
<222> LOCATION: (33)..(33)
<223> OTHER INFORMATION: X is N, P, D, or S
<220> FEATURE:
<221> NAME/KEY: MISC_FEATURE
<222> LOCATION: (34)..(34)
<223> OTHER INFORMATION: X is F, or Y
<220> FEATURE:
<221> NAME/KEY: MISC_FEATURE
<222> LOCATION: (40)..(40)
<223> OTHER INFORMATION: X is Q, or H
<220> FEATURE:
<221> NAME/KEY: MISC_FEATURE
<222> LOCATION: (41)..(41)
<223> OTHER INFORMATION: X is H, D, Y, or N
<220> FEATURE:
<221> NAME/KEY: MISC_FEATURE
<222> LOCATION: (43)..(43)
<223> OTHER INFORMATION: X is G, or D
<220> FEATURE:
<221> NAME/KEY: MISC_FEATURE
<222> LOCATION: (45)..(45)
<223> OTHER INFORMATION: X is A, or V
<220> FEATURE:
<221> NAME/KEY: MISC_FEATURE
<222> LOCATION: (47)..(47)
<223> OTHER INFORMATION: X is K, or R
<220> FEATURE:
<221> NAME/KEY: MISC_FEATURE
<222> LOCATION: (49)..(49)
<223> OTHER INFORMATION: X is M, I, or L
<220> FEATURE:
<221> NAME/KEY: MISC_FEATURE
<222> LOCATION: (50)..(50)
<223> OTHER INFORMATION: X is I, or L
<220> FEATURE:
<221> NAME/KEY: MISC_FEATURE
<222> LOCATION: (51)..(51)
<223> OTHER INFORMATION: X is Y, or F
<220> FEATURE:
<221> NAME/KEY: MISC_FEATURE
<222> LOCATION: (52)..(52)
<223> OTHER INFORMATION: X is E, D, Y, A, or G
<220> FEATURE:
<221> NAME/KEY: MISC_FEATURE
<222> LOCATION: (53)..(53)
<223> OTHER INFORMATION: X is V, A, or G
<220> FEATURE:
<221> NAME/KEY: MISC_FEATURE
<222> LOCATION: (54)..(54)
<223> OTHER INFORMATION: X is S, T, N, H, G, I, or R
<220> FEATURE:
<221> NAME/KEY: MISC_FEATURE
<222> LOCATION: (55)..(55)
<223> OTHER INFORMATION: X is K, or N
<220> FEATURE:
<221> NAME/KEY: MISC_FEATURE
<222> LOCATION: (57)..(57)
<223> OTHER INFORMATION: X is P, or A
<220> FEATURE:
<221> NAME/KEY: MISC_FEATURE
<222> LOCATION: (61)..(61)
<223> OTHER INFORMATION: X is P, S, or T
<220> FEATURE:
<221> NAME/KEY: MISC_FEATURE
<222> LOCATION: (62)..(62)
<223> OTHER INFORMATION: X is D, N, A, or S
<220> FEATURE:
<221> NAME/KEY: MISC_FEATURE
<222> LOCATION: (66)..(66)
```

```
<223> OTHER INFORMATION: X is G, or A
<220> FEATURE:
<221> NAME/KEY: MISC_FEATURE
<222> LOCATION: (67)..(67)
<223> OTHER INFORMATION: X is S, or A
<220> FEATURE:
<221> NAME/KEY: MISC_FEATURE
<222> LOCATION: (70)..(70)
<223> OTHER INFORMATION: X is G, or D
<220> FEATURE:
<221> NAME/KEY: MISC_FEATURE
<222> LOCATION: (71)..(71)
<223> OTHER INFORMATION: X is N, S, or T
<220> FEATURE:
<221> NAME/KEY: MISC_FEATURE
<222> LOCATION: (74)..(74)
<223> OTHER INFORMATION: X is S, or F
<220> FEATURE:
<221> NAME/KEY: MISC_FEATURE
<222> LOCATION: (77)..(77)
<223> OTHER INFORMATION: X is I, or V
<220> FEATURE:
<221> NAME/KEY: MISC_FEATURE
<222> LOCATION: (78)..(78)
<223> OTHER INFORMATION: X is S, or T
<220> FEATURE:
<221> NAME/KEY: MISC_FEATURE
<222> LOCATION: (81)..(81)
<223> OTHER INFORMATION: X is Q, or L
<220> FEATURE:
<221> NAME/KEY: MISC_FEATURE
<222> LOCATION: (82)..(82)
<223> OTHER INFORMATION: X is A, T, S, or P
<220> FEATURE:
<221> NAME/KEY: MISC_FEATURE
<222> LOCATION: (83)..(83)
<223> OTHER INFORMATION: X is E, or D
<220> FEATURE:
<221> NAME/KEY: MISC_FEATURE
<222> LOCATION: (86)..(86)
<223> OTHER INFORMATION: X is A, or S
<220> FEATURE:
<221> NAME/KEY: MISC_FEATURE
<222> LOCATION: (87)..(87)
<223> OTHER INFORMATION: X is D, H, Q, or I
<220> FEATURE:
<221> NAME/KEY: MISC_FEATURE
<222> LOCATION: (89)..(89)
<223> OTHER INFORMATION: X is Y, or H
<220> FEATURE:
<221> NAME/KEY: MISC_FEATURE
<222> LOCATION: (94)..(94)
<223> OTHER INFORMATION: X is S, R, A, T, or G
<220> FEATURE:
<221> NAME/KEY: MISC_FEATURE
<222> LOCATION: (95)..(95)
<223> OTHER INFORMATION: X is S, G, R, or absent
<220> FEATURE:
<221> NAME/KEY: MISC_FEATURE
<222> LOCATION: (96)..(96)
<223> OTHER INFORMATION: X is S, M, P, or absent
<220> FEATURE:
<221> NAME/KEY: MISC_FEATURE
<222> LOCATION: (97)..(97)
<223> OTHER INFORMATION: X is G, S, P, T, N, or E
<220> FEATURE:
<221> NAME/KEY: MISC_FEATURE
<222> LOCATION: (98)..(98)
<223> OTHER INFORMATION: X is S, H, G, T, N, or P
<220> FEATURE:
<221> NAME/KEY: MISC_FEATURE
<222> LOCATION: (99)..(99)
<223> OTHER INFORMATION: X is T, Q, A, P, G, V, K, or absent
<220> FEATURE:
<221> NAME/KEY: MISC_FEATURE
<222> LOCATION: (100)..(100)
<223> OTHER INFORMATION: X is R, S, T, G, L, K, N, H, A, or absent
<220> FEATURE:
<221> NAME/KEY: MISC_FEATURE
```

-continued

```
<222> LOCATION: (101)..(101)
<223> OTHER INFORMATION: X is L, or V
<220> FEATURE:
<221> NAME/KEY: MISC_FEATURE
<222> LOCATION: (102)..(102)
<223> OTHER INFORMATION: X is V, L, or I
<220> FEATURE:
<221> NAME/KEY: MISC_FEATURE
<222> LOCATION: (108)..(108)
<223> OTHER INFORMATION: X is K, or Q

<400> SEQUENCE: 21

Gln Xaa Xaa Leu Thr Gln Pro Xaa Ser Xaa Ser Xaa Ser Pro Gly Gln
1               5                   10                  15

Ser Xaa Thr Xaa Ser Cys Thr Gly Xaa Xaa Xaa Asp Val Gly Xaa Xaa
            20                  25                  30

Xaa Xaa Val Ser Trp Tyr Gln Xaa Xaa Pro Xaa Lys Xaa Pro Xaa Leu
        35                  40                  45

Xaa Xaa Xaa Xaa Xaa Xaa Xaa Arg Xaa Ser Gly Val Xaa Xaa Arg Phe
        50                  55                  60

Ser Xaa Xaa Lys Ser Xaa Xaa Thr Ala Xaa Leu Thr Xaa Xaa Gly Leu
65                  70                  75                  80

Xaa Xaa Xaa Asp Glu Xaa Xaa Tyr Xaa Cys Ser Ser Tyr Xaa Xaa Xaa
                85                  90                  95

Xaa Xaa Xaa Xaa Xaa Xaa Phe Gly Gly Gly Thr Xaa Leu Thr Val Leu
            100                 105                 110

<210> SEQ ID NO 22
<211> LENGTH: 124
<212> TYPE: PRT
<213> ORGANISM: Artificial Sequence
<220> FEATURE:
<223> OTHER INFORMATION: hm7 cons VH

<400> SEQUENCE: 22

Glu Val Gln Leu Leu Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Leu Glu Gly Gly Gly Arg Tyr Tyr Asp Phe Trp Ser Ala Asp
            100                 105                 110

Tyr Trp Gly Gln Gly Thr Leu Val Thr Val Ser Ser
        115                 120

<210> SEQ ID NO 23
<211> LENGTH: 14
<212> TYPE: PRT
<213> ORGANISM: Artificial Sequence
<220> FEATURE:
<223> OTHER INFORMATION: CS19ME LCDR1 AA

<400> SEQUENCE: 23

Thr Gly Thr Ser Ser Asp Val Gly Gly Tyr Asn Phe Val Ser
```

1                    5                    10

<210> SEQ ID NO 24
<211> LENGTH: 7
<212> TYPE: PRT
<213> ORGANISM: Artificial Sequence
<220> FEATURE:
<223> OTHER INFORMATION: CS19ME LCDR2

<400> SEQUENCE: 24

Ala Val Ser Lys Arg Pro Ser
1               5

<210> SEQ ID NO 25
<211> LENGTH: 11
<212> TYPE: PRT
<213> ORGANISM: Artificial Sequence
<220> FEATURE:
<223> OTHER INFORMATION: CS19ME LCDR3

<400> SEQUENCE: 25

Ser Ser Tyr Ser Ser Glu Ser Thr Arg Val Val
1               5                    10

<210> SEQ ID NO 26
<211> LENGTH: 111
<212> TYPE: PRT
<213> ORGANISM: Artificial Sequence
<220> FEATURE:
<223> OTHER INFORMATION: CS19ME VL

<400> SEQUENCE: 26

Gln Ser Ala Leu Thr Gln Pro Arg Ser Val Ser Gly Ser Pro Gly Gln
1               5                    10                  15

Ser Val Thr Ile Ser Cys Thr Gly Thr Ser Ser Asp Val Gly Gly Tyr
            20                  25                  30

Asn Phe Val Ser Trp Tyr Gln Gln His Pro Gly Lys Ala Pro Lys Leu
        35                  40                  45

Leu Ile Tyr Ala Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ser Ser Glu
                85                  90                  95

Ser Thr Arg Val Val Phe Gly Gly Gly Thr Lys Leu Thr Val Leu
            100                 105                 110

<210> SEQ ID NO 27
<211> LENGTH: 124
<212> TYPE: PRT
<213> ORGANISM: Artificial Sequence
<220> FEATURE:
<223> OTHER INFORMATION: CS19ME3-23 VH

<400> SEQUENCE: 27

Glu Val Gln Leu Leu Glu Ser Gly Gly Gly Leu Val Gln Pro Gly Gly
1               5                    10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val

```
        50              55              60
```

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Leu Glu Gly Gly Gly Arg Tyr Tyr Asp Phe Trp Ser Ala Asp
            100                 105                 110

Tyr Trp Gly Gln Gly Thr Leu Val Thr Val Ser Ser
        115                 120

<210> SEQ ID NO 28
<211> LENGTH: 333
<212> TYPE: DNA
<213> ORGANISM: Artificial Sequence
<220> FEATURE:
<223> OTHER INFORMATION: CS19ME VL NA
<220> FEATURE:
<221> NAME/KEY: misc_feature
<222> LOCATION: (67)..(108)
<223> OTHER INFORMATION: LCDR1 coding sequence
<220> FEATURE:
<221> NAME/KEY: misc_feature
<222> LOCATION: (154)..(174)
<223> OTHER INFORMATION: LCDR2 coding sequence
<220> FEATURE:
<221> NAME/KEY: misc_feature
<222> LOCATION: (271)..(303)
<223> OTHER INFORMATION: LCDR3 coding sequence

<400> SEQUENCE: 28
cagtctgccc tgactcagcc tcgctcagtg tccgggtctc ctggacagtc agtcaccatc      60
tcctgcactg gaaccagcag tgatgttggt ggttataact ttgtctcctg gtaccaacag     120
cacccaggca agcccccaa actcctgatt tatgctgtca gtaagcggcc ctcaggggtc       180
cctgatcgct tctctggctc caagtctggc aacacggcct ccctgacaat ctctgggctc     240
caggctgagg acgaggctga ttattactgc agctcatatt caagcgagag cactagggtg     300
gttttcggcg gagggaccaa gctgaccgtc cta                                   333

<210> SEQ ID NO 29
<211> LENGTH: 372
<212> TYPE: DNA
<213> ORGANISM: Artificial Sequence
<220> FEATURE:
<223> OTHER INFORMATION: CS19ME3-23 VH NA
<220> FEATURE:
<221> NAME/KEY: misc_feature
<222> LOCATION: (91)..(105)
<223> OTHER INFORMATION: HCDR1 coding sequence
<220> FEATURE:
<221> NAME/KEY: misc_feature
<222> LOCATION: (148)..(198)
<223> OTHER INFORMATION: HCDR2 coding sequence
<220> FEATURE:
<221> NAME/KEY: misc_feature
<222> LOCATION: (295)..(339)
<223> OTHER INFORMATION: HCDR3 coding sequence

<400> SEQUENCE: 29
gaggtgcagc tgttggagtc tggggggaggc ttggtacagc ctggggggtc cctgagactc      60
tcctgtgcag cctctggatt caccttcagt agctatgcta tgcactgggt ccgccaggct     120
ccaggcaagg ggctggagtg ggtggcagtt atatcatatg atggaagcaa taaatactac     180
gcagactccg tgaagggccg attcaccatc tccagagaca attccaagaa cacgctgtat     240
ctgcaaatga acagcctgag agctgaggac acggctgtgt attactgtgc gactctcgag     300
```

-continued

```
ggaggggggac ggtattacga tttttggagc gctgactact ggggccaggg aaccctggtc      360
accgtctctt ca                                                           372
```

<210> SEQ ID NO 30
<211> LENGTH: 14
<212> TYPE: PRT
<213> ORGANISM: Artificial Sequence
<220> FEATURE:
<223> OTHER INFORMATION: CS19ME-N LCDR1

<400> SEQUENCE: 30

```
Thr Gly Thr Ser Ser Asp Val Gly Gly Tyr Asn Phe Val Ser
1               5                   10
```

<210> SEQ ID NO 31
<211> LENGTH: 7
<212> TYPE: PRT
<213> ORGANISM: Artificial Sequence
<220> FEATURE:
<223> OTHER INFORMATION: CS19ME-N LCDR2

<400> SEQUENCE: 31

```
Ala Val Ser Asn Arg Pro Ser
1               5
```

<210> SEQ ID NO 32
<211> LENGTH: 11
<212> TYPE: PRT
<213> ORGANISM: Artificial Sequence
<220> FEATURE:
<223> OTHER INFORMATION: CS19ME-N LCDR3

<400> SEQUENCE: 32

```
Ser Ser Tyr Ser Ser Glu Ser Thr Arg Val Val
1               5                   10
```

<210> SEQ ID NO 33
<211> LENGTH: 111
<212> TYPE: PRT
<213> ORGANISM: Artificial Sequence
<220> FEATURE:
<223> OTHER INFORMATION: CS19ME-N VL

<400> SEQUENCE: 33

```
Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
                20                  25                  30

Asn Phe Val Ser Trp Tyr Gln Gln His Pro Gly Lys Ala Pro Lys Leu
            35                  40                  45

Leu Ile Tyr Ala Val Ser Asn Arg Pro Ser Gly Val Pro Asp Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ser Ser Glu
                85                  90                  95

Ser Thr Arg Val Val Phe Gly Gly Gly Thr Lys Leu Thr Val Leu
            100                 105                 110
```

<210> SEQ ID NO 34
<211> LENGTH: 124
<212> TYPE: PRT

```
<213> ORGANISM: Artificial Sequence
<220> FEATURE:
<223> OTHER INFORMATION: CS19ME3-30-N VH

<400> SEQUENCE: 34

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Leu Glu Gly Gly Gly Arg Tyr Tyr Asp Phe Trp Ser Ala Asp
            100                 105                 110

Tyr Trp Gly Gln Gly Thr Leu Val Thr Val Ser Ser
        115                 120

<210> SEQ ID NO 35
<211> LENGTH: 333
<212> TYPE: DNA
<213> ORGANISM: Artificial Sequence
<220> FEATURE:
<223> OTHER INFORMATION: CS19ME-N VL NA
<220> FEATURE:
<221> NAME/KEY: misc_feature
<222> LOCATION: (67)..(108)
<223> OTHER INFORMATION: LCDR1 coding sequence
<220> FEATURE:
<221> NAME/KEY: misc_feature
<222> LOCATION: (154)..(174)
<223> OTHER INFORMATION: LCDR2 coding sequence
<220> FEATURE:
<221> NAME/KEY: misc_feature
<222> LOCATION: (271)..(303)
<223> OTHER INFORMATION: LCDR3 coding sequence

<400> SEQUENCE: 35
cagtctgccc tgactcagcc tcgctcagtg tccgggtctc ctggacagtc agtcaccatc      60
tcctgcactg gaaccagcag tgatgttggt ggttataact ttgtctcctg gtaccaacag     120
cacccaggca agcccccaa actcctgatt tatgctgtca gtaaccggcc ctcaggggtc      180
cctgatcgct tctctggctc caagtctggc aacacggcct ccctgacaat ctctgggctc     240
caggctgagg acgaggctga ttattactgc agctcatatt caagcgagag cactagggtg     300
gttttcggcg gagggaccaa gctgaccgtc cta                                  333

<210> SEQ ID NO 36
<211> LENGTH: 372
<212> TYPE: DNA
<213> ORGANISM: Artificial Sequence
<220> FEATURE:
<223> OTHER INFORMATION: CS19ME3-30-N VH NA
<220> FEATURE:
<221> NAME/KEY: misc_feature
<222> LOCATION: (91)..(105)
<223> OTHER INFORMATION: HCDR1 coding sequence
<220> FEATURE:
<221> NAME/KEY: misc_feature
<222> LOCATION: (148)..(198)
<223> OTHER INFORMATION: HCDR2 coding sequence
```

-continued

```
<220> FEATURE:
<221> NAME/KEY: misc_feature
<222> LOCATION: (295)..(339)
<223> OTHER INFORMATION: HCDR3 coding sequence

<400> SEQUENCE: 36
caggtgcagc tggtggagtc tggggggaggc gtggtacagc ctgggcggtc cctgagactc        60
tcctgtgcag cctctggatt caccttcagt agctatgcta tgcactgggt ccgccaggct       120
ccaggcaagg ggctggagtg ggtggcagtt atatcatatg atggaagcaa taaatactac       180
gcagactccg tgaagggccg attcaccatc tccagagaca attccaagaa cacgctgtat       240
ctgcaaatga acagcctgag agctgaggac acggctgtgt attactgtgc gactctcgag       300 ggaggggac ggtattacga tttttggagc gctgactact ggggccaggg aaccctggtc       360
accgtctctt ca                                                           372
```